(12) United States Patent
Möhwald et al.

(10) Patent No.: US 6,242,561 B1
(45) Date of Patent: Jun. 5, 2001

(54) SUBSTITUTED POLYTHIOPHENES, PROCESSES FOR THEIR PREPARATION THEIR USE

(75) Inventors: Helmut Möhwald, Annweiler (DE); Vladimir Belov, St. Petersburg (RU); Wolfgang Schrof, Neuleiningen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/142,201

(22) PCT Filed: Mar. 6, 1997

(86) PCT No.: PCT/EP97/01140

§ 371 Date: Jan. 8, 1999

§ 102(e) Date: Jan. 8, 1999

(87) PCT Pub. No.: WO97/32914

PCT Pub. Date: Sep. 12, 1997

(30) Foreign Application Priority Data

Mar. 6, 1996 (DE) .............................. 196 08 701

(51) Int. Cl.[7] .................... C08G 75/00; C08G 75/04
(52) U.S. Cl. .................. 528/377; 528/373; 528/485; 540/1; 548/117; 427/407.1
(58) Field of Search .................... 528/377, 373, 528/485; 540/1; 548/117; 427/407.1

(56) References Cited

U.S. PATENT DOCUMENTS

| | | | |
|---|---|---|---|
| 4,959,430 | 9/1990 | Jonas et al. | 526/257 |
| 4,987,042 | 1/1991 | Jonas et al. | 429/213 |
| 5,035,926 | 7/1991 | Jonas et al. | 427/393 |

FOREIGN PATENT DOCUMENTS

| | | |
|---|---|---|
| 339340 | 11/1989 | (EP) . |
| 332704 | 12/1994 | (EP) . |
| 60120722 | 12/1983 | (JP) . |
| 63244578 | 4/1990 | (JP) . |

OTHER PUBLICATIONS

Prasad et al., *Intro. to NLO effects . . .* , 1991.
Arsalani et al. *J. Prak. Chem.* 337 (1995), pp. 1–11.
Kricheldorf, *Handbook of Polymer Syntheses,* part B, pp. 1383–1390, 1992.
*J. Org. Chem.* 1995, 60, pp. 6813–6819.
*Bull. de la Soc. Chim. de France,* 1986, No. 2, pp. 267–275.
*Bull. de la Soc. Chim. de France,* 1983, No. 5–6, pp. II 159–II 163.
Pomerantz, *Synthetic Metals,* 55–57, 1993, pp. 960–965.
*J. Chem. Soc. Comm,* 1992, No. 22, pp. 1672–1673.
Pomerantz, *Synthetic Metals,* 41–43 (1991), pp. 825–830.
Berggren et al., *Nature,* 372, 1994, pp. 444–446.
Stille, *Agnew. Chem. Int. Ed. Engl.,* 25, pp. 508–542, 1986.
Bao et al., *J. Am. Chem. Soc.,* 117, pp. 12426–12435, 1995.

*Primary Examiner*—Duc Truong
(74) *Attorney, Agent, or Firm*—Keil & Weinkauf

(57) ABSTRACT

Novel polythiophene-containing structural units of the general formulae (I) and (II)

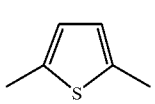

(I)

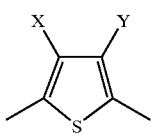

(II)

processes for their preparation, monomers for their preparation, their use in various industrial fields, and an electrically conductive material comprising these.

11 Claims, No Drawings

SUBSTITUTED POLYTHIOPHENES, PROCESSES FOR THEIR PREPARATION THEIR USE

The present invention relates to a polythiophene, comprising structural units of the general formulae (I) and (II)

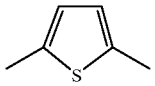

(I)

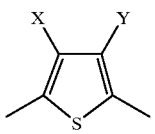

(II)

where X and Y independently of one another can be identical or different and are a linear or branched-chain $C_1$- to $C_{22}$-alkyl group; a linear or branched-chain $C_1$- to $C_{22}$-alkoxy group; a linear or branched-chain $C_1$- to $C_{22}$-alkoxyalkyl group; a linear or branched-chain $C_1$- to $C_{22}$-acyl group; a linear or branched-chain $C_1$- to $C_{22}$-thioacyl group; a linear or branched-chain $C_1$- to $C_{22}$-acyloxy group; a linear or branched-chain $C_1$- to $C_{22}$-thioacyloxy group; a $C_5$- to $C_8$-cycloalkyl group, a $C_6$- to $C_{18}$-aryl group or a $C_5$- to $C_8$-heterocyclic group, which in each case can in turn be substituted by one or more linear or branched-chain $C_1$- to $C_{22}$-alkyl group(s), one or more linear or branched-chain $C_1$- to $C_{22}$-alkoxy group(s), one or more linear or branched-chain $C_1$- to $C_{22}$-alkoxyalkyl group(s), one or more linear or branched-chain $C_1$- to $C_{22}$-acyl group(s) or one or more linear or branched-chain $C_1$- to $C_{22}$-thioacyl group(s); $NO_2$; or $NHR^1$, where $R^1$ may be identical or different and is hydrogen or a linear or branched-chain $C_1$- to $C_{22}$-alkyl group, a linear or branched-chain $C_1$- to $C_{22}$-alkoxy group, a linear or branched-chain $C_1$- to $C_{22}$-alkoxyalkyl group, a linear or branched-chain $C_1$- to $C_{22}$-acyl group or a linear or branched-chain $C_1$- to $C_{22}$-thioacyl group, or X and Y, together with the atoms to which they are bonded, form a carbon-containing ring system which beside carbon contains nitrogen (N), oxygen (O), sulfur (S) or phosphorus (P) heteroatoms or mixtures of two or more of these heteroatoms, where this ring system can in turn be substituted on the carbon atom(s), the nitrogen atom(s) or the phosphorus atom(s) in each case by a group Z, where each Z independently of one another is a group as defined above for X and Y, or two adjacent groups Z together form a radical represented by one of the following general formulae (III) to (VI)

(III)

(IV)

(V)

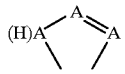

(VI)

where A is carbon (C), nitrogen (N), phosphorus (P) or mixtures of two or more of these atoms,
where, if A is carbon, each of these As can either carry a hydrogen atom or can in turn be substituted as defined above for X and Y, obtainable by the Stille reaction, wherein 2,5-dihalothiophene or 2,5-ditriflatethiophene and thiophene derivatives which are bis(trialkyltin)-substituted on the carbon atoms adjacent to the sulfur, which correspond to the structural unit (II) defined above, or 2,5 bis(trialkyltin) thiophene and thiophene derivatives which are bis(halo)- or bis(triflate)-substituted on the carbon atoms adjacent to the sulfur, which correspond to the structural unit (II) defined above, are reacted with one another in suitable solvents in the presence of suitable Pd(0) or Pd(II) complexes or salts thereof as catalyst, or the Suzuki reaction, wherein 2,5-dihalo- or 2,5-triflate-substituted thiophenes, which correspond to the structural unit (II) according to the invention, are reacted with thiophenediboric acid or thiophenediboric acid esters in the presence of a base and of a palladium complex of the structure $PdL_4$ (L=ligand), wherein the diboric acid (ester) derivatives of the thiophene derivatives corresponding to the above structural units (II) are reacted with 2,5-dihalo- or 2,5-triflate-substituted thiophene in the presence of a base and a palladium complex, as defined above.

It further relates to processes and monomers for their preparation, to their use in various industrial fields, and to an electrically conductive material which contains at least one polythiophene according to the invention.

Polythiophenes are an important class of conjugated polymers having high electrical conductivity and nonlinear optical properties and can be used as materials for semiconductors (see, inter alia, EP-B-0 332 704 and P. N. Prasad, D. J. Williams "Introduction to NLO effects in molecules and polymers", John Wiley and Sons, Inc. (1991)). The polythiophenes furthermore have electrochromic and antistatic properties (see N. Arsalani and K. E. Geckeler "Conducting isopolymers: preparation, properties, and applications", J. Prakt. Chem. 337 (1995, pp. 1–11)).

Until now, almost exclusively homopolymers of thiophene or substituted thiophenes were known. In this case, usually only simple 3-alkyl- or 3,4-dialkylthiophenes were polymerized and investigated with respect to possible industrial applications. A review of the polythiophenes prepared to date and the most frequently used processes for their preparation is given by Hans R. Kricheldorf "Handbook of polymer synthesis", Part B, pp. 1383–1390 (1992), M. Pomerantz "Processable polymers and copolymers of 3-alkylthiophenes and their blends", Synthetic Metals, 41-43 (1991), pp. 825–830, and EP-A-0 339 340.

The J 60 120 722 relates to linear copolymers comprising 5-membered heterocyclic compounds having functional groups being selected among halogen, hydroxy, amino or carbohydrate groups, as defined therein. These copolymers are produced by anodic oxidation.

The JP 63 344 578 relates to the preparation of an electrically conductive polymer being constituted of 3,4-substituted heterocyclic 5-membered ring compounds, by means of a polymerization in the presence of an oxidizing agent, such as iron chloride, in an organic solvent.

α-Stannylthiophen of formula (n-butyl)$_3$Sn(C$_4$H$_2$S)$_3$—Sn(n-butyl)$_3$ is disclosed in J.Org.Chem. 1995, 60, pp. 6813–6819.

2,5-Dibromo-3,4-diacetaminothiophene and its preparation is disclosed in "Bulletin de la Société Chimique de France, 1986, no. 2, pp. 267–275".

The "Bulletin de la Société Chimique de France, 198 3, no. 5–6, pp. II 159-II 163" discloses non-substituted Thieno [3,4-b]pyrazine as well as the in 2- or 3- or in 2- and 3-position by a methyl group substituted derivative thereof, as well as their preparation.

Soluble poly(2,3-dihexylthieno[3,4-b]pyrazines) were prepared by M. Pomerantz et al. by iron chloride/oxygen polymerization of the corresponding monomers (see M. M. Pomerantz "New processable low band-gap, conjugated polyheterocycles", Synthetic Metals, 55–57, pp. 960–965 (1993), and J. Chem. Soc. Commun. 1992, pp. 1672–73). By means of this process, only doped substances can be prepared. Even after treatment with aqueous ammonia or hydrazine, an EPR signal and line widening in the NMR spectra were observed, which points to the presence of paramagnetic species.

As processes for their preparation, until now mainly chemical (e.g. by means of $FeCl_3$) or electrochemical oxidation of a single precursor or of a mixture of two different 3-alkylthiophenes (see M. Pomerantz "Processable polymers and copolymers of 3-alkylthiophenes and their blends" Synthetic Metals, 41–43 (1991), pp. 825–830, in particular p. 828, and M. Berggren et al. "Light-emitting diodes with variable colours from polymer blends", Nature 372 (1994), pp. 444–446, in particular p. 444), were carried out with formation of the corresponding polymers linked in the 2,5-position.

A further, general starting point for the preparation of oligo- or polythiophenes includes the catalytic coupling of organometallic reagents (usually Grignard reagents) (see Kricheldorf, loc. sit.).

It is to be taken into account here, however, that thiophenes with functional groups, such as, for example, nitro, carbonyl, imino, amido, nitrile, pyridine and pyrazine groups, cannot be employed in this process.

A relatively new process for the preparation of new C—C linkages is the Stille reaction. According to this reaction, an organic electrophile is reacted with an organotin reagent in the presence of a suitable solvent and of a Pd(0) or Pd(II) complex (see J. K. Stille "The palladium-catalyzed cross-coupling reactions of organotin reagents with organic electrophiles", Angew. Chem. Int. Ed. Engl. 25, pp. 508–542 (1986)). This reaction has already been successfully carried out for the preparation of poly(2,5-thieno-1,4-phenylenes) according to the following scheme (see Z. Bao et al., J. Am. Chem. Soc., 117, 12426–12435 (1995)).

In general, the doping leads to new electronic states, which are desirable for certain applications, such as, for example, relatively high electrical conductivity, but are undesirable for other applications, such as, for example, the preparation of thin films having good optical quality. The properties of doped materials often change as a function of time. Furthermore, the reproducibility of their properties is in general also lower compared with the properties of undoped substances.

The demands which are placed on electrically conductive materials continually increase. The polythiophenes known until now are not always able to meet these demands.

These considerations show, for example, the necessity of developing novel, hitherto unknown doped and undoped copoly- and co-oligothiophenes which contain both substituted and unsubstituted structural units. Such materials, which compared with the homopolythiophenes prepared until now, have different and improved properties, should be utilizable in various industrial fields, such as, for example, as substances having semiconductor, electrochromic or antistatic properties or as dyes absorbing in the near infrared region.

The object of the present invention is thus the provision of novel polythiophenes which have more than one structural unit, which units are different from one another, and can be used advantageously in various industrial areas as outlined above.

We have found that this object is achieved by the polythiophenes according to the invention described in detail in the following text.

The structural unit (I) present in the polythiophenes according to the invention is derived from thiophene.

In the structural unit (II), in which X and Y, if they do not, together with the atoms to which they are bonded, form a carbon-containing ring system, can be the group mentioned at the outset, it is preferred that X and Y are identical. If X and Y are each the group $NHR^1$, the two radicals $R^1$ are preferably also identical. Under the alkyl, alkoxy, alkoxyalkyl, acyl and thioacyl groups with 1 to 22 C-atoms, as listed above, those having 1 to 20 carbon atoms are preferred, those having 6 to 20 carbon atoms are more preferred, those having 10 to 16 carbon atoms particularly preferred.

Particularly preferred X and Y substituents are the acyl groups, thioacyl groups and $NHR^1$ defined above.

In the context of the present invention, the expression "thioacyl group" designates a group of the general formula —C(S)-R, where R is alkyl. The expression "heterocyclic group", as mentioned at the outset, designates alicyclic saturated, alicyclic unsaturated and aromatic heterocyclic groups.

Furthermore, X and Y, together with the atoms to which they are bonded, can form a carbon-containing ring system which beside carbon contains nitrogen (N), oxygen (O), sulfur (S) or phosphorus (P) heteroatoms or mixtures of two or more of these heteroatoms. Preferably X and Y in this case form a divalent radical which has two to eight atoms, additionally preferably three to six atoms, and, together with the two atoms to which it is bonded, forms a ring system having four to ten or five to eight atoms. The number of heteroatoms defined above possibly present in this ring system is preferably up to three, additionally preferably up to two. Among the heteroatoms defined above, nitrogen (N) is preferred. Preferably, the ring system described above is a system having at least one, additionally preferably two or more double bonds. In particularly preferred embodiments of the present invention, the double bonds of the above ring system are conjugated with the double bonds of the thiophene fragment to which the ring system is bonded, and, if appropriate, to the double bonds of further radicals of the formulae (III) to (VI), as defined in claim 1, bonded to the ring system described above.

This ring system can in turn be substituted on the carbon, nitrogen or phosphorus atoms, in each case by a group Z, where each Z independently of one another is a group as defined above for X and Y, and here too the substituents preferably indicated for X and Y are in turn to be regarded as preferred.

Two adjacent groups Z can moreover together form a radical which is selected from among the radicals of the general formulae (III) to (IV) mentioned at the outset, the symbol "A" being carbon (C), nitrogen (N), phosphorus (P) or mixtures of two or more or these atoms, it being possible, if A is carbon, for this either to carry a hydrogen atom or in turn, as defined above for X and Y, to be substituted. In this case, these radicals, together with the atoms to which they are bonded, form a further ring which forms a conjugated, unsaturated system, preferably with the other rings in the structural unit.

Preferred rings resulting in this case which may be mentioned is the cyclobutene ring.

A preferred group of the polythiophenes according to the invention are those having structural units of the general formulae (VII) and/or (VIII)

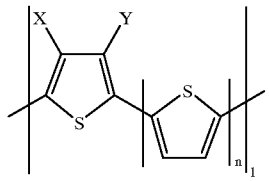

(VII)

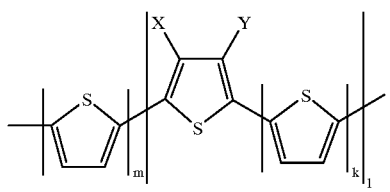

(VIII)

where X and Y are as defined above and n, m and k independently of one another are an integer from 1 to 10, preferably an integer from 1 to 6, and l is an integer from 1 to 3000, preferably 1 to 1000, in particular 1 to 100. In this case, the alternating sequence of a substituted thiophene unit and an unsubstituted thiophene unit is preferred.

Particularly preferred polythiophenes are those in which the structural unit (II) is selected from the group consisting of the radicals of the following general formulae

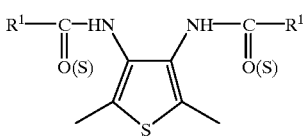

(IIa)

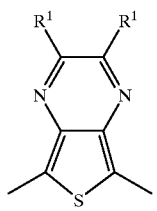

(IIb)

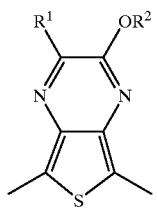

(IIc)

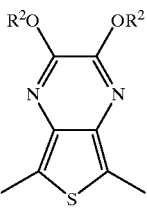

(IId)

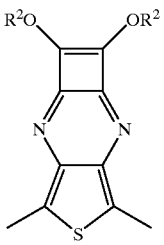

(IIe)

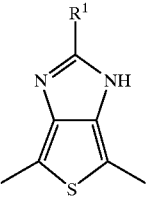

(IIf)

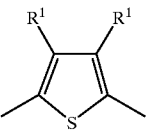

(IIg)

wherein $R^2$ is $CH_2R^1$ or $R^2$ is $CHR^1_2$, $R^1$ is H or as defined in claim 1, under the proviso that radicals of the general formula (IIg) wherein $R^1$ being hydrogen are excluded.

Among the abovementioned structural units (II), the following, individually listed structural units are particularly preferred. In this case it is obvious that these are derived from the corresponding compounds which are disubstituted in the neighborhood of the thiophene sulfur atom:

3,4-di(decyl)thiophene, 3,4-di(undecyl)thiophene, 3,4-di(dodecyl)thiophene, 3,4-di(tridecyl)thiophene, 3,4-di(tetradecyl)thiophene, 3,4-di(pentadecyl)thiophene, 3,4-di(hexadecyl)thiophene, 3,4-di(heptadecyl)thiophene and 3,4-di(octadecyl)thiophene structural units;

3,4-di(decyloxy)thiophene, 3,4-di(undecyloxy)thiophene, 3,4-di-(dodecyloxy)thiophene, 3,4-di(tridecyloxy)thiophene, 3,4-di-(tetradecyloxy)thiophene, 3,4-di(pentadecyloxy)thiophene, 3,4-di-(hexadecyloxy)thiophene, 3,4-di(heptadecyloxy)thiophene and 3,4-di-(octadecyloxy)thiophene structural units; furthermore preferred are structural units in which the ether radicals defined above are replaced by the corresponding thio-ether radicals;

3,4-di(decyloxyethyl)thiophene, 3,4-di(undecyloxyethyl)thiophene, 3,4-di-(dodecyloxyethyl)thiophene, 3,4-di(tridecyloxyethyl)thiophene, 3,4-di(tetradecyloxyethyl)thiophene, 3,4-di(pentadecyloxyethyl)thiophene, 3,4-di-(hexadecyloxyethyl)thiophene, 3,4-di (heptadecyloxyethyl)thiophene and 3,4-di-(octadecyloxyethyl)thiophene structural units; further structural units being preferred in which the oxygen atom(s) in the alkyloxyalkyl groups defined in greater detail above is in the 3-, 3,6-, 3,6,9-, 3,6,9,12-position, etc., depending on the total length of the substituent, such as, for example, 3,4-di((2-decyloxy)ethyl) thiophene; 3,4-di((3-decyloxy)propyl)thiophene; 3,4-di((4-decyloxy)butyl)thiophene; etc.; 3,4-di(2-(2-(decyloxyethoxyl)ethyl)thiophene; 3,4-di(2-(2-(undecyloxyethoxyl)ethyl)thiophene; 3,4-di(2-(2-(dodecyloxy)ethoxy)ethyl)thiophene; etc.; the total number of C atoms not exceeding 22; furthermore preferred are structural units in which the oxygen atom of the alkyloxyalkyl substituents defined above is replaced by sulfur;

3,4-di(cyclopentyl)thiophene, 3,4-di(cyclopentenyl) thiophene, 3,4-di(cyclohexy1)thiophene, 3,4-di (cyclohexenyl)thiophene, 3,4-di(cyclohexadienyl) thiophene, 3,4-di(phenyl)thiophene and 3,4-di(benzyl) thiophene structural units, it being possible for the substituents indicated above in turn to be substituted by one or more of the groups defined for $R^1$;

3,4-di(decanoyl)thiophene, 3,4-di(undecanoyl)thiophene, 3,4-di(dodecanoyl)thiophene, 3,4-di(tridecanoyl) thiophene, 3,4-di(tetradecanoyl)thiophene, 3,4-di (pentadecanoyl)thiophene, 3,4-di(hexadecanoyl) thiophene, 3,4-di(heptadecanoyl)thiophene and 3,4-di (octadecanoyl)thiophene structural units; as well as the corresponding alkanoyloxy structural units, such as 3,4-di(decanoyloxy)thiophene, 3,4-di(undecanoyloxy) thiophene; etc.; furthermore preferred here are also substituents which the carbonyl group therein is replaced by a thiocarbonyl group;

3,4-di(decanoylamino)thiophene, 3,4-di(undecanoylamino)thiophene, 3,4-di(dodecanoylamino)thiophene, 3,4-di(tridecanoylarnino)thiophene, 3,4-di(tetradecanoylamino)thiophene, 3,4-di(pentadecanoylamino)thiophene, 3,4-di(hexadecanoylamino)thiophene, 3,4-di(heptadecanoylamino)thiophene and 3,4-di(octadecanoylamino)thiophene structural units, it being possible here too for the oxygen atom to be replaced by sulfur;

2,3-dipentylthienol[3,4-b]pyrazine, 2,3-didecylthieno[3,4-b]pyrazine, 2,3-diundecylthieno[3,4-b]pyrazine, 2,3-didodecylthieno[3,4-b]pyrazine, 2,3-ditridecylthieno[3,4-b]pyrazine, 2,3-ditetradecylthieno[3,4-b]pyrazine, 2,3-dipentadecylthieno[3,4-b]pyrazine, 2,3-dihexadecylthieno[3,4-b]pyrazine, 2,3-diheptadecylthieno[3,4-b]pyrazine and 2,3-dioctadecylthieno[3,4-b]pyrazine structural units; 2-methyl-3-decyloxythieno[3,4-b]pyrazine-, 2-methyl-3-undecyloxythieno[3,4-b]pyrazine-, 2-methyl-3-dodecyloxythieno[3,4-b]pyrazine-, 2-methyl-3-tridecyloxythieno[3,4-b]pyrazine-, 2-methyl-3-tetradecyloxythieno[3,4-b]pyrazine-, 2-methyl-3-pentadecyloxythieno[3,4-b]pyrazine-, 2-methyl-3-hexadecyloxythieno[3,4-b]pyrazine-, 2-methyl-3-octadecyloxythieno[3,4-b]pyrazine-, 2-methyl-3-eicosyloxythieno[3,4-b]pyrazine-, 2-methyl-3-docosyloxythieno[3,4-b]pyrazine-, 2-ethyl-3-decyloxythieno[3,4-b]pyrazine-2-ethyl-3-undecyloxythieno[3,4-b]pyrazine-, 2-ethyl-3-dodecyloxythieno[3,4-b]pyrazine-, 2-ethyl-3-tridecyloxythieno[3,4-b]pyrazine-, 2-ethyl-3-tetradecyloxythieno[3,4-b]pyrazine-, 2-ethyl-3-pentadecyloxythieno[3,4-b]pyrazine-, 2-ethyl-3-hexadecyloxythieno[3,4-b]pyrazine-, 2-ethyl-3-octadecyloxythieno[3,4-b]pyrazine-, 2-ethyl-3-eicosyloxythieno[3,4-b]pyrazine-, 2-ethyl-3-docosyloxythieno[3,4-b]pyrazine-Struktureinheiten,2-phenyl3-decyloxythieno[3,4-b]pyrazine-, 2-phenyl-3-undecyloxythieno[3,4-b]pyrazine-, 2-phenyl-3-dodecyloxythieno[3,4-b]pyrazine-, 2-phenyl-3-tridecyloxythieno[3,4-b]pyrazine-, 2-phenyl-3-tetradecyloxythieno[3,4-b]pyrazine-, 2-phenyl-3-pentadecyloxythieno[3,4-b]pyrazine-, 2-phenyl-3-hexadecyloxythieno[3,4-b]pyrazine-, 2-phenyl-3-heptadecyloxythieno[3,4-b]pyrazine-, 2-phenyl-3-octadecyloxythieno[3,4-b]pyrazine-, 2-phenyl-3-eicosyloxythieno[3,4-b]pyrazine- und 2-phenyl-3-docosyloxythieno[3,4-b]pyrazine-Struktureinheiten, it beeing possible here too for the oxygen atom to be replaced by sulfur;

2,3-di(decyloxy)thieno[3,4-b]pyrazine, 2,3-di(undecyloxy)thieno[3,4-b]pyrazine, 2,3-di(dodecyloxy)thieno[3,4-b]pyrazine, 2,3-di(tridecyloxy)thieno[3,4-b]pyrazine, 2,3-di(tetradecyloxy)thieno[3,4-b]pyrazine, 2,3-di(pentadecyloxy)thieno[3,4-b]pyrazine, 2,3-di(hexadecyloxy)thieno[3,4-b]pyrazine, 2,3-di(heptadecyloxy)thieno[3,4-b]pyrazine and 2,3-di(octadecyloxy)thieno[3,4-b]pyrazine, 2,3-di(eicosyloxy)thieno[3,4-b]pyrazine and 2,3-di(docosyloxy)thieno[3,4-b]pyrazine structural units; furthermore preferred are structural units in which the ether radicals defined above are replaced by the corresponding thioether radicals; 2,3-di(decyloxyethyl)thieno[3,4-b]pyrazine, 2,3-di(undecyloxyethyl)thieno[3,4-b]pyrazine, 2,3-di(dodecyloxyethyl)thieno[3,4-b]pyrazine, 2,3-di(tridecyloxyethyl)thieno[3,4-b]pyrazine, 2,3-di(tetradecyloxyethyl)thieno[3,4-b]pyrazine, 2,3-di(pentadecyloxyethyl)thieno[3,4-b]pyrazine, 2,3-di(hexadecyloxyethyl)thieno[3,4-b]pyrazine, 2,3-di(heptadecyloxyethyl)thieno[3,4-b]pyrazine and 2,3-di(octadecyloxyethyl)thieno[3,4-b]pyrazine structural units; structural units furthermore being preferred in which the oxygen atoms in the alkoxyalkyl groups defined in greater detail above are e.g. 3-, 3,6-, 3,6,9-, 3,6,9,12-position, etc., depending on the total length of the substituent; such as, for example, 2,3-di(ethyl-2-oxydecyl)thieno[3,4-b] pyrazine; 2,3-di(propyl-3-oxydecyl)thieno[3,4-b] pyrazine; 2,3-di(butyl-4-oxydecyl)thieno[3,4-b] pyrazine, etc., the total numbers of the C atoms not exceeding 22; furthermore preferred are structural units in which the oxygen atom of the alkoxyalkyl substituents defined above is replaced by sulfur;

2,3-di(cyclopentyl)thieno[3,4-b]pyrazine, 2,3-di(cyclopentenyl)thieno[3,4-b]pyrazine, 2,3-di(cyclohexyl)thieno[3,4-b]pyrazine, 2,3-di(cyclohexenyl)thieno[3,4-b]pyrazine, 2,3-di(cyclohexadienyl)thieno[3,4-b]pyrazine, 2,3-di(phenyl)thieno[3,4-b]pyrazine and 2,3-di(benzyl)thieno[3,4-b]pyrazine structural units, it being possible for the substituents indicated above in turn to be substituted by one or more of the groups defined for $R^1$;

5,6-di(decyloxy)cyclobuta[b]thieno[3,4-e]pyrazine, 5,6-di(undecyloxy)cyclobuta[b]thieno[3,4-e]pyrazine, 5,6-di(dodecyloxy)cyclobuta[b]thieno [3,4-e]pyrazine, 5,6-di(tridecyloxy)cyclobuta[b]thieno[3,4-e]pyrazine, 5,6-di(tetradecyloxy)cyclobuta[b]thieno[3,4-e]

pyrazine, 5,6-di(pentadecyloxy)cyclobuta[b]thieno[3,4-e]pyrazine, 5,6-di(hexadecyloxy)cyclobuta[b]thieno[3,4-e]pyrazine, 5,6-di(heptadecyloxy)cyclobuta[b]thieno[3,4-e]pyrazine and 5,6-di(octadecyloxy)cyclobuta[b]thieno[3,4-e]pyrazine structural units; furthermore preferred are structural units in which the ether radicals defined above are replaced by the corresponding thioether radicals;

5,6-di(cyclopentyloxy)cyclobuta[b]thieno[3,4-e]pyrazine, 5,6-di(cyclopentenyloxy)cyclobuta[b]thieno[3,4-e]pyrazine, 5,6-di(cyclohexyloxy)cyclobuta[b]thieno[3,4-e]pyrazine, 5,6-di(cyclohexenyloxy)cyclobuta[b]thieno[3,4-e]pyrazine, 5,6-di(cyclohexadienyloxy)cyclobuta[b]thieno[3,4-e]pyrazine, 5,6-di(phenyl)cyclobuta[b]thieno[3,4-e]pyrazine and 5,6-di(benzyl)cyclobuta[b]thieno[3,4-e]pyrazine structural units, it being possible for the substituents indicated above in turn to be replaced by one or more of the groups defined for $R^1$;

2-decyl-1H-thieno[3,4-d]imidazole, 2-undecyl-1H-thieno[3,4-d]imidazole, 2-dodecyl-1H-thieno[3,4-d]imidazole, 2-tridecyl-1H-thieno[3,4-d]imidazole, 2-tetradecyl-1H-thieno[3,4-d]imidazole, 2-pentadecyl-1H-thieno[3,4-d]imidazole, 2-hexadecyl-1H-thieno[3,4-d]imidazole, 2-heptadecyl-1H-thieno[3,4-d]imidazole and 2-octadecyl-1H-thieno[3,4-d]imidazole structural units;

2-cyclopentyl-1H-thieno[3,4-d]imidazole, 2-cyclopentenyl-1H-thieno[3,4-d]imidazole, 2-cyclohexyl-1H-thieno[3,4-d]imidazole, 2-cyclohexenyl1H-cyano[3,4-d]imidazole, 2-cylohexadienyl-1H-thieno[3,4-d]imidazole, 2-phenyl-1H-thieno[3,4-d]imidazole and 2-benzyl-1H-thieno[3,4-d]imidazole structural units; 2-butylthio-1H-thieno[3,4-d]imidazol-, 2-pentylthio-1H-thieno[3,4-d]imidazol-, 2-hexylthio-1H-thieno[3,4-d]imidazol-, 2-heptylthio-1H-thieno[3,4-d]imidazol-, 2-octylthio-1H-thieno[3,4-d]imidazol-, 2-nonylthio-1H-thieno[3,4-d]-imidazol-, 2-decylthio-1H-thieno[3,4-d]imidazol-, 2-undecylthio1H-thieno[3,4-d]imidazol-, 2-dodecylthio-1H-thieno[3,4-d]imidazol-, 2-tridecylthio-1H-thieno[3,4-d]imidazol-, 2-tetradecylthio-1H-thieno[3,4-d]imidazol-, 2-pentadecylthio-1H-thieno[3,4-d]imidazol-, 2-hexadecylthio-1H-thieno[3,4-d]imidazol-, 2-heptadecylthio-1H-thieno[3,4-d]imidazol-, 2-octodecylthio-1H-thieno[3,4-d]imidazol structural unitsn, wherein the obove mentioned substituents may be again substituted by one or more of the groups defined as $R^1$.

The proportions of the structural units (I) and (II) defined above in the polythiophenes according to the invention is from approximately 1 to approximately 99 mol % (I) and from approximately 99 to approximately 1 mol % (II), preferably from approximately 30 to approximately 70 mol % (I) and from approximately 70 to approximately 30 mol % (II) and in particular from approximately 50 mol % (I) to approximately 50 mol % (II), the proportions of these two structural units in each case adding up to 100 mol %. Preferably the sequence of the two structural units (I) and (II) is alternating.

The weight average molecular weight ($M_w$) of the polythiophenes prepared according to the invention, measured by gel permeation chromatography using polystyrene as a standard, is in general from approximately 1000 to approximately 500,000, preferably from approximately 10,000 to approximately 250,000, and in particular from approximately 30,000 to approximately 80,000. The inhomogeneity of the molecular weight distribution, ie. the quotient of the weight average molecular weight and the number average molecular weight ($M_w/M_n$), is from approximately 2 to approximately 4, preferably from approximately 2 to approximately 3, and in particular from approximately 2 to approximately 2.5.

The processes for preparing the polythiophenes according to the invention are the reaction according to Stille, which has already been mentioned in the introduction, and the reaction according to Suzuki (see A. Suzuki et al., "Stereoselective synthesis of arylated (E)-alkenes by the reaction of alk-1-enylboranes with aryl halides in the presence of palladium catalyst", J.C.S. Chem. Comm., 1979, pp. 866–867) which will be explained in greater detail in the following.

In the Suzuki reaction, 2,5-dihalo- or 2,5-triflate-substituted thiophenes, which correspond to the structural unit (II) according to the invention, are reacted with thiophenediboric acid or thiophenediboric acid esters in the presence of a base, preferably sodium ethoxide, and of a palladium complex of the structure $PdL_4$ (L=ligand), preferably $Pd(PPh_3)_4$.

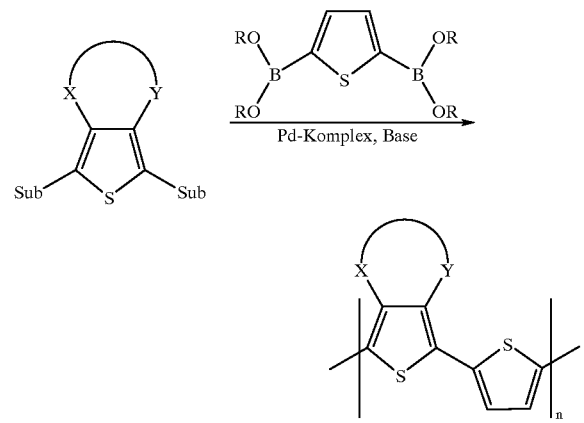

Sub = halogen or triflate
X, Y = as defined above
R = H or alkyl

Preferred boranes employed in this reaction are thiophene-2,5-diboric acid and esters thereof. With respect to further details of this reaction, reference is made to the literature source referred to above.

Of course, in the context of the Suzuki reaction, the diboric acid (ester) derivatives of the thiophene derivatives corresponding to the above structural units (II) are reacted with 2,5-dihalo- or 2,5-triflate-substituted thiophene which corresponds to the structural unit (I).

The particularly preferred process for preparing the polythiophenes according to the invention, however, is the Stille reaction already mentioned at the outset. In this reaction, 2,5-dihalothiophene or 2,5-ditriflatethiophene and thiophene derivatives which are bis(trialkyltin)-substituted on the carbon atoms adjacent to the sulfur, which correspond to the structural unit (II) defmed above, or 2,5 bis(trialkyltin) thiophene and thiophene derivatives which are bis(halo)- or bis(triflate)-substituted on the carbon atoms adjacent to the sulfur, which correspond to the structural unit (II) defmed in claim 1, are reacted with one another according to the following scheme in suitable solvents in the presence of suitable Pd(0) or Pd(II) complexes or salts thereof as catalyst.

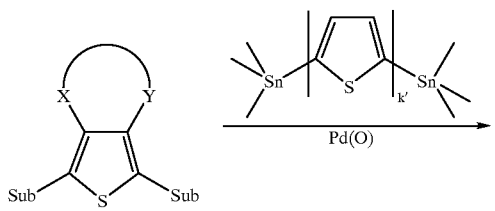
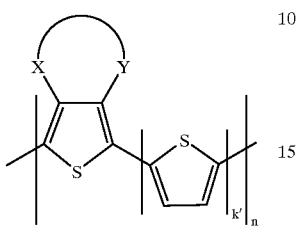

k = 1, 2, 3, ..., 10
Sub = halogen or triflate

Among the substituents "Sub" mentioned in the above scheme, halogen-substituted derivatives are preferably employed. If bis(triflate)-, ie. (CF$_3$SO$_3$)-substituted starting materials are employed, LiCl, for example, can be added to improve the reactivity.

On account of the mild conditions for carrying it out, this reaction tolerates all types of substituents, such as, for example, amine, acyl, ester, ether and nitro groups.

The catalysts employed are Pd(II) or Pd(0) complexes. Preferred catalysts which may be mentioned are, in particular, the following: tris(dibenzylideneacetone)dipalladium (Pd$_2$dba$_3$), Pd(Ph$_3$P)$_2$Cl$_2$, "Ph" being C$_6$H$_5$, and Pd(Ph$_3$P)$_4$. When using tris(dibenzylideneacetone)dipalladium, various ligands can be added, the catalytically active catalyst PdL$_4$ being formed in situ by ligand exchange between the weakly coordinated Pd2dba$_3$ and the ligand(s). The ligands used in this case are PPh$_3$, AsPH$_3$,[2-(CH$_3$)C$_6$H$_4$]$_3$P, P(OPh)$_3$ and (2-furyl)$_3$P, "furyl" being a 2-furyl group. The amount of the catalyst employed is from approximately 2 to approximately 10 mol %, preferably about 2 to about 5 mol %, based on the amount of bis(trialkyltin)-substituted starting material employed.

Although in general all solvents which are able to keep the starting materials and catalysts employed in solution can be employed, DMF, NMP and cyclic ethers, such as, for example, THF and dioxane, are the most suitable solvents. Among these, DMF and THF are preferably employed.

The reaction is in general carried out at temperatures between room temperature and the boiling point of the solvent, temperatures from approximately 50° C. to approximately 100° C. being preferred. Depending on the starting materials and/or catalysts used, the reaction time varies between 1 day and 1 month, preferably 1 day to 1 week.

As a result of this relatively mild reaction, it is possible to prepare polythiophenes having the following advantageous properties:
- the thiophenes obtained exhibit only slight or no structural defects, doping or overoxidation;
- it is possible to employ a great multiplicity of functional groups including acceptors, donors and π-systems having several bonds between carbon and a heteroatom; and
- it is possible to prepare strictly alternating copolythiophenes having various substituted rings, for example to carry out the reaction of thiophenes substituted in the 3- and 4-positions with unsubstituted thiophenes, which with the processes generally used previously for polythiophene preparation was only possible with extreme difficulty.

Although the Suzuki reaction also has the abovementioned advantages compared with the conventional methods, in the context of the present invention the Stille reaction is particularly preferred since, in contrast to the Suzuki reaction, it needs no additional base.

The present invention furthermore provides compounds of the general formulae (IXa) to (IXc)

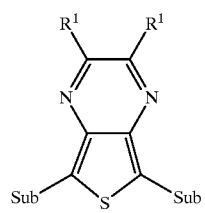

IXa

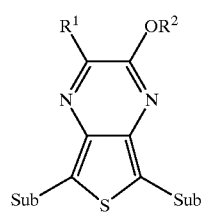

IXb

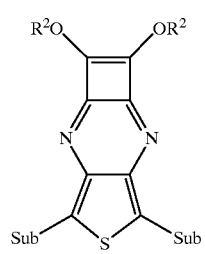

IXc in which "Sub" is hydrogen (H), bromine (Br), chlorine (Cl), iodine (I), triflate (CF3SO$_3$) or trialkyltin, and R$^1$ is as defined above, and R$^2$ is CH$_2$R$^1$ or CHR$^1_2$, under the proviso that, if in compound IXa both "Sub" are identical and respectively hydrogen, R$_1$ may not have the following meaning:

R$_1$ are identical and represent hydrogen, methyl or C$_6$H$_{13}$
R$_1$ are different from each other and represent methyl and hydrogen.

Additionally, N,N-substituted 3,4-diamino-2,5-dihalo- (or ditriflate)thiophenes of the general formula (X)

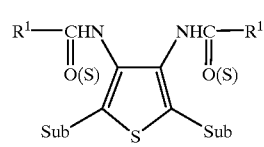

(X)

in which "Sub" and R$^2$ are as defined above, are provided.

As substituents "Sub", the abovementioned halogen radicals are preferred, furthermore preferred are iodine or bromine. With respect to preferred radicals R$^1$, reference is made to the listing given further above.

Although this class of monomer can in general be prepared according to conventional processes for the preparation of such compounds, the general process for the preparation of the monomers according to the invention illustrated in the examples is preferably used.

Thin films of the polythiophenes according to the invention can be prepared by pouring carefully filtered or centrifuged solutions in chloroform or trichloroethylene onto a glass substrate. By means of this process, homogeneous films having a thickness of up to 300 nm can be obtained. The optical quality of the films is high and exhibits no noticeable scattering of the light. In particular, the polymers containing alternating structural units (I) and (II) have a maximum in the absorption spectrum at approximately 850 to approximately 900 nm and have a high transparency in the visible range, having a weaker maximum at approximately 420 nm and a minimum at approximately 520 nm. These values were measured in THF, in which these substances have a green color. The same is true of films obtained from these polymers. Polymers having amide or sulfamide substituents have the red color typical of polythiophenes ($\lambda_{max}$= 410 to 430 nm), both as films and in THF solutions.

The positions of the maxima in the long-wave region of the solutions or films of all copolymers which contain thieno[3,4-b]pyrazine units IIb to IIe is determined by their relative proportion and is in the range from approximately 400 to approximately 1000, particularly approximately 410 to approximately 900 nm.

The polythiophenes described herein can be used either undoped or doped for the antistatic finishing of substances which do not or only poorly conduct electrical current, as electrically conductive films, as semiconductor films, as additive for active electrodes, for LEDs, as organic transistors and capacitors. In this connection, these copolymers are processed in the customary manner and, if appropriate, mixed with known additives and formulating substances which are necessary for the particular application or processed according to known processes.

Moreover, the present invention additionally provides a process for the antistatic finishing of substances which do not or only poorly conduct electrical current by applying a layer comprising an electrically conductive organic polymers to the surface of the substrates, which comprises producing on the surface of the substrates by polymerization a layer of at least one polythiophene which contains the structural units of the general formulae (I) and (II) defined above.

The above-mentioned layer may be also exclusively composed of the above defined conductive oganic polymer.

The present invention furthermore provides an electrically conductive material which contains at least one polythiophene according to the present invention.

The present invention will now be illustrated further in some selected examples.

EXAMPLES

Model Investigations on Some Preferred Polythiophenes According to the Invention The advantages of the novel strategy for the provision of electrically conductive polymers based on copolythiophenes realized in the context of the present invention will be illustrated in detail again in the following with the aid of some model substances.

2,3-Didecylthieno[3,4-b]pyrazine-thiophene oligomer

In order to obtain the co-oligomers or copolymers according to the invention, the components 1 and 3 were reacted in THF in the presence of $(Ph_3P)_4Pd$ or $(Ph_3P)_2PdCl_2$, which was used in a catalytic amount of from 2 to 5 mol %, based on the component 1 shown in the scheme below. With the dibromide 1 shown below, the reaction began at room temperature.

In order to obtain more accurate information with respect to the structures of the polymers obtained, it was necessary first to investigate the structure of the oligomers formed in the initial stage of the polymerization. An investigation of this type is in general possible if a starting material is employed in excess and the reaction is interrupted at a low conversion rate. An example of a reaction of this type is shown below.

7=M*580, $\lambda_{max}$ 503 nm

8=M*662, $\lambda_{max}$ 530 nm

9=M*1070, $\lambda_{max}$ 617 nm

In this scheme, m and k are each an integer of 1 to 10 and 1 is an integer of 1 to 3000, R is alkyl, $\lambda_{max}$ is the wavelength of the maximum absorption in the visible range.

"Short" oligomers 7, 8 and 9 were separated from the reaction mixture and obtained as pure compounds after separation by means of a silica gel column. A fraction of "longer oligomers" which was obtained after separation was investigated by mass spectroscopy using matrix-asssted laser-

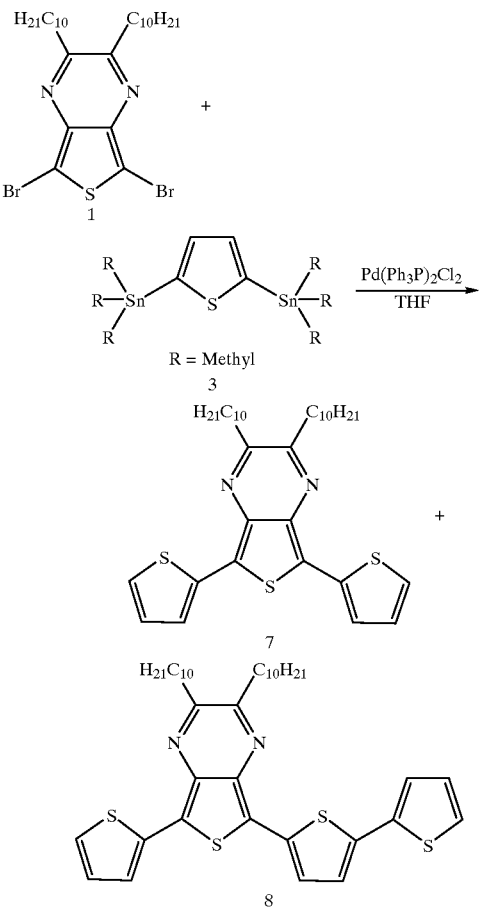

-continued

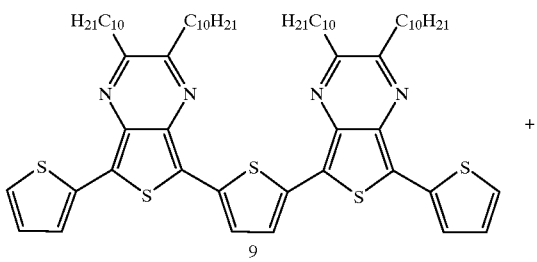

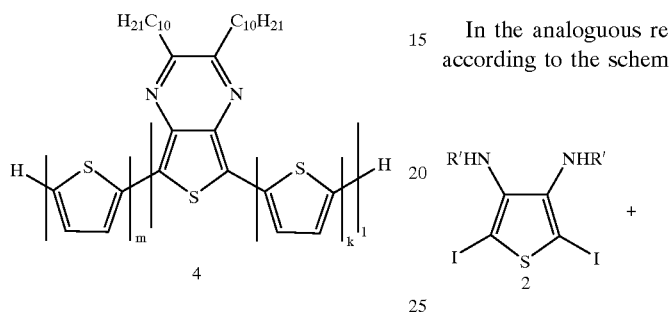

desorption ionization (MALDI). Using this method it is possible to obtain the mass of the intact molecules without decomposition thereof. In this context it is to be noted that during the separation on the silica gel column the tin residues still present in the oligomers are removed. The results of the mass-spectroscopic investigations are shown in Table 1 below.

are brought to reaction. After the purification, in this embodiment polymers are obtained whose elemental analysis approximately has a 1:1 ratio of the two monomers. The weight average molecular weight ($M_w$) of the polymers of the general formula 4 obtained starting from 1 and 3 which are obtained in the context of this reaction is from approximately 20,000 to approximately 100,000, preferably approximately 50,000, in each case measured by GPC using polystyrene as a standard. The polydispersity ($M_w/M_n$) is from approximately 2.0 to approximately 3.0, preferably from approximately 2.0 to 2.5.

In the analoguous reactions of further copolythiophenes according to the scheme below

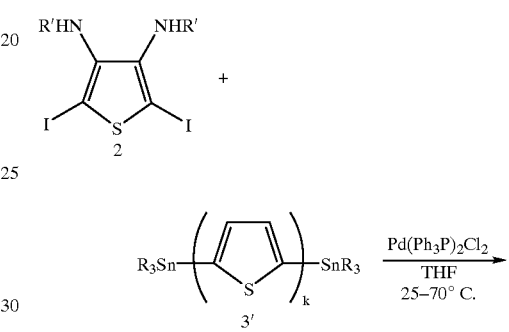

TABLE 1

| MALDI mass spectrum of oligomer 4 as a mixed fraction | | | | | | | | |
|---|---|---|---|---|---|---|---|---|
| 4 | 1 | 2 | 3 | 4 | 5 | 6 | 7 | 8 |
| M* | 1160 | 1242 | 1324 | 1574 | 1656 | 1738 | 2070 | 2154 |
| Σl | 2 | 2 | 2 | 3 | 3 | 3 | 4 | 4 |
| Σ(k + m) | 4 | 5 | 6 | 4 | 5 | 6 | 5 | 6 |
| m/k, possible values | 1/1,2 | 1/2,2 | 1/2,3 | 1/1,1,1 | 1/1,1,2 | 1/1,2,2 or 1,1,3 | 1/1,1,1,1 | 1/1,1,1,2 |
| | 2/1,1 | 2/1,2 | 2/2,2 | | 2/1,1,1 | 2/1,1,2 | | 2/1,1,1,1 |
| | | | 3/1,2 | | | 3/1,1,1 | | |
| Relative intensity | 1.5 | 0.85 | 0.30 | 2.4 | 1.15 | 0.30 | 0.45 | 0.15 |

Note:
M* = Relative monoisotopic molecular weight

As a comparison of the masses obtained in the series 4, 1-2-3; 4-5-6; and 7-8, which in each case have the same number of thieno[3,4-b]pyrazine units (Σl=2,3,4), no regular alternation between the 3,4 unsubstituted thiophene rings and the thieno[3,4-b]pyrazine rings exists in this reaction, in which one of the educts was employed in an excess. In some cases the pyrazine rings are separated from one another by more than one thiophene ring. Thus, for example, the molecular weight 1738 corresponds to three thienopyrazine fragments (Σl=3) and six thiophene rings (Σ(k+m)=6). As Σk≧Σl, the values possible for m are 1,2 and 3. If m is 1, the set of k values can be 1,2,2 or 1,1,3, rearrangements being possible within the first set which then lead to a set 2,1,2 or 2,2,1, which correspond to three isomeric oligomers.

This type of "homocoupling" takes place less markedly if equal molar amounts of the two starting materials (1 and 3)

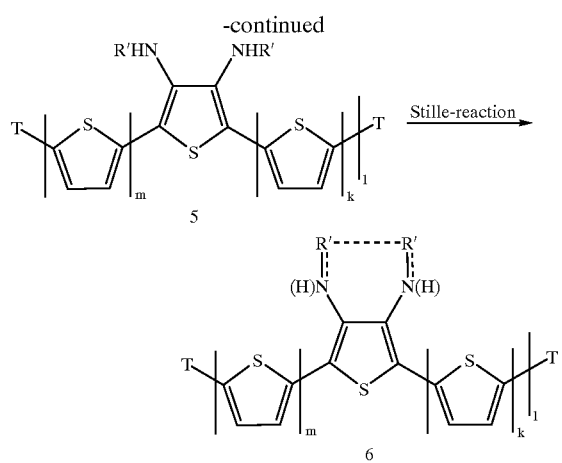

-continued

T = H or trialkyltin
m, k and l = as defined above
R = alkyl, preferably CH₃
R' = alkanoyl having 16 to 22 C atoms,

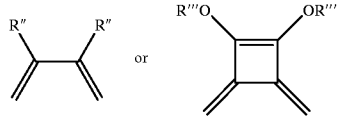

R'' = alkyl or alkoxy having 10 to 22 C-atoms,
R''' = alkyl having 10 to 22 C-atoms.

copolythiophenes having a weight average molecular weight from approximately 30,000 to approximately 60,000, preferably to approximately 50,000, and a polydispersity of from approximately 2.0 to approximately 3.0 are obtained.

These polythiophenes of the general formulae 4, 5 and 6 with alkyl (or alkoxyalkyl) substituents having 10 to 22 carbon atoms are soluble in organic solvents, such as, for example, chloroform and THF.

In all these cases, of course, the alternating sequence between substituted and unsubstituted thiophene is preferred.

A further, very interesting modification of the thieno[3,4-b]pyrazine fragment includes the extension of the conjugation within the pyrazine component to be polymerized. This additional conjugated system can be heterocyclic or nonheterocyclic. In the latter case, it can be constructed of one, two or more C=C double bonds with formation of 4-, 6-, etc.-membered rings. The 4-membered ring system of cyclobuta[b]thieno[3,4-e]pyrazine 10 is of particular interest, as it represents a novel unusual polythiophene type having a special electron density distribution and thus novel physical properties.

General Process for the Preparation of the Monomers According to the Invention 5,7-Dibromothieno[3,4-b]pyrazines of the general formula 11, which are interesting monomers for the synthesis of undoped or doped poly- and oligothiophenes of the general formulae 4 and 6, as defined above, are preferably obtained as follows:

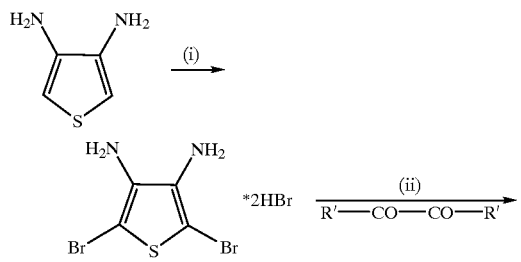

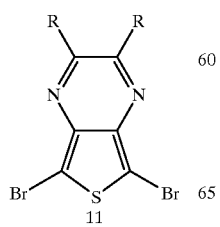

-continued

R' = H, C₁- to C₂₂-alkyl or C₁- to C₂₂-alkoxyalkyl
i: Reaction with a bromine-dioxane complex in THF,
ii: Reaction of R¹—CO—CO—R¹ in the presence of triethylamine in a solvent mixture of ethanol and methylene chloride The synthesis of 3,4-diaminothiophene is described in the literature (see F. Outurquin et al. "Synthéses du diamino-3,4 thiophène de quelques dérivés de substitution", Bulletin de la Société Quimique de France 1983, pp. II-153 to II-158 and WO 87/05296). Alkyl- or alkoxyalkyl-substituted 1,2-diketones can be obtained in a simple manner by oxidation of acetylene (see D. G. Lee "The preparation of α-diones. Phase-transfer assisted oxidation of alkynes by potassium permanganate", Synthesis, 1978, pp. 462–463). The reaction is illustrated by the following scheme.

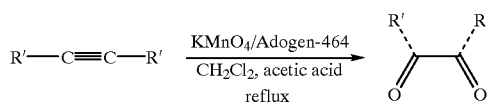

Preferred embodiments of the above monomer 11 are the monomers of the general formulae 14 and 17 described below.

The 2,3-dialkoxy-5,7-dihalothieno[3,4-b]pyrazines of the general formula 14 can be obtained as follows:

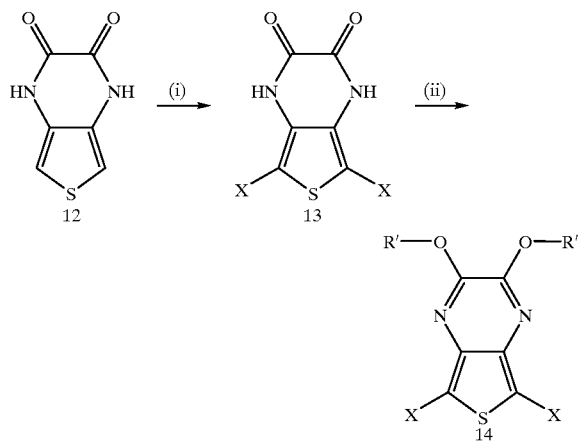

i: Br₂-dioxane (1:1) complex, THF, -10° C. to room temperature (X = Br), or I₂/KIO₃/aq. H₂SO₄/AcOH/CCl₄, reflux (X = I)
ii: RCH₂I, Ag₂CO₃, toluene, room temperature, reflux, ultrasound,
R' = as defined above,
X = halogen 2-alkyl(aryl)-3-alkoxy-5,7-dibromothieno[3,4-e]pyrazines may be synthesized as follows:

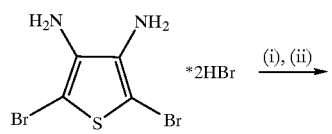

-continued

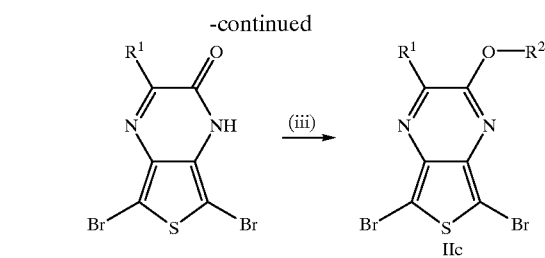

i: 2 mol Et₃N, abs. EtOH, 0° C.;
ii: R¹COCO₂R³ or R¹COCOOH (R¹ = H, or as defined in claim 1, particularly alkyl or aryl, as defined therein, R³ = alkyl), 16 h, room temperature
iii: R²I (R² = CH₂R¹ or CHR¹₂), Ag₂CO₃, toluene, 20 to 110° C., ultrasonic.

The most important intermediate for synthesizing IIc, compound 10 (3-alkyl-5,7-dibromo-1,2-dihydro-2-oxothieno[3,4-e]pyrazine) is similar to the compound as obtained by starting from 3,4-diaminothiophene and ethylpyruvate by F. Outurquin, P. Lerouge and C. Palmier (Bull., Soc. Chem. Fr., 1086, 2, pp. 267–275). However, the product described therein comprised no bromine atoms and their further chemical conversion is different from the reactions carried out herein.

The 5,6-dialkoxy-1,3-dibromocyclobuta(b)thieno[3,4-e] pyrazines of the general formula 17 can be obtained as follows:

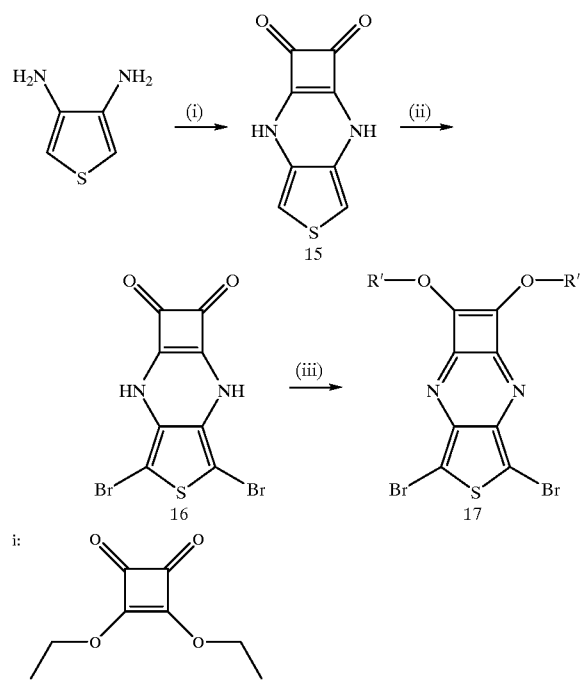

i:

abs. EtOH, room temperature
ii: Br₂-dioxane (1:1) complex, THF, -10° C. to room temperature
iii: R'CH₂I, Ag₂CO₃, toluene, room temperature, reflux, ultrasound
R' = linear or branched-chain C₁- to C₂₂-alkyl The 5,7-dibromo- or 5,7-diiodo-1,2,3,4-tetrahydro-2,3-dioxothieno[3,4-b] pyrazines 13 can be obtained starting from the known compound 12 (see F.Outurquin et al., Bull. Chem. Soc. France 1983, 5-6, 11-153–II-154) in a yield of 60 to 90% as a yellowish-brown to dark brown powder. It has an extremely low solubility in virtually all solvents, but its quality can be checked by microanalysis for the Br or I content (see F. Outurquin et al., loc. cit.)

The monomers 14 and 17 can be prepared starting from the amides 13 or the compounds 16 by O,O'-alkylation with the corresponding iodides (RCH₂I) under similar conditions indicated in G. C. Hopkins et al., J. Org. Chem. 32, p. 4040 (1967). When using the silver salts of the amides, O,O'-alkylation predominates compared with an N,N'-alkylation if the reaction is carried out in an aprotic nonpolar solvent, preferably in a hydrocarbon. Toluene is particularly preferably used, as it permits a reaction at higher temperatures. It is necessary to carry out the reaction with normal stirring and to treat with ultrasound at specific time intervals in order to accelerate the rate of the heterogeneous reaction. Under these conditions, the reaction proceeds completely within a few days, and a yield of approximately 40% to approximately 70% is obtained. Products to be attributed to N,N'- and O,O'-alkylation were not isolated. The starting compound 15 is obtained in a simple manner and high yield starting from 3,4diaminothiophene and commercially available 1,2-diethoxy-2,3-dioxocyclobutene according to the process described by A. H. Schmidt et al. in Synthesis, p. 869 (1978). The bromination and O,O'-dialkylation are then carried out in the same manner as described above and the monomer 17 is obtained.

The isolation and purification of the monomers 14 and 17 is carried out by chromatography on a silica gel column and subsequent recrystallization. The compounds obtained are stable in air at room temperature. Their thermal stability is also adequate for the subsequent reactions, and no degradation in solution was observed at temperatures up to 100–120° C. under a protective gas atmosphere over several hours.

A further interesting class of monomer are the N,N-substituted 3,4-diamino-2,5-diiodothiophenes of the general formula 18. These can be obtained as follows:

(5)

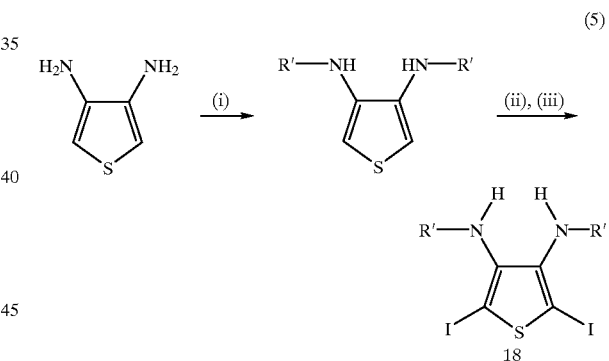

i: RCOCl or RSO₂Cl or RCSCl, pyridine
ii: I₂/KIO₃, AcOH/H₂SO₄/CCl₄, reflux
iii: (only if R' = RC(O)): Lawesson's reagent, toluene, reflux
R' = RC(O), RSO₂, RC(S) where R = linear or branched-chain C₁- to C₂₂-alkyl or linear or branched-chain C₁- to C₂₂-alkoxyalkyl.

Starting Compounds and Monomers According to the Invention

Docosane-11,12-dione

3H₂₁C₁₀—C≡C—C₁₀H₂₁+4KMnO₄+2 H₂O
3H₂₁C₁₀—CO—CO—C₁₀H₂₁+4MnO₂+4KOH

11-Docosyne was oxidized according to the general process shown above (D. G. Lee et al., Synthesis, 1978, pp. 462–463). 11-Docosyne (prepared according to the process described by T. M. Fyles in J. Org. Chem. 1984, pp. 753–761) (15.3 g, 0.05 mol) and Adogen® 464 (5.7 g, obtainable from ALDRICH) were dissolved in a mixture of 360 ml of dichloromethane and 18 ml of glacial acetic acid. Potassium permanganate (21.6 g, 0.136 mol) was finely powdered and added to the solution which was kept at reflux and vigorously stirred. This mixture was stirred under reflux for four hours. The excess of oxidant and the precipitated manganese dioxide were destroyed by addition of a solution of sodium nitrite or sulfite and treatment with dilute mineral acid until complete decolorization took place. The organic layer was separated off and the aqueous layer was extracted with dichloromethane. The combined organic layers were washed in succession with water, 2% strength NaOH, water and sodium chloride solution. After drying over magnesium sulfate, the organic solvent was evaporated and the resulting waxy substance was recrystallized from methanol. 10.8 g (64% of theory) of docosane-11,12-dione were obtained as a pale yellow solid having a melting point of 68.5–69° C.

3,4-Diamino-2,5-dibromothiophene (dihydrobromide)

3,4-Diaminothiophene (prepared according to the process of F. Outurquin already described above) (1.14 g, 10 mmol) was dissolved in 30 ml of dry THF under a nitrogen atmosphere. 4.96 g (20 mmol of bromine-1,4-dioxane (1:1) complex were then added to the stirred solution in small portions at −10° C. This became black, and a black solid precipitated. The reaction mixture was allowed to warm to room temperature and it was stirred for two hours. Dry diethyl ether was then added (100 ml), and the precipitate was separated off, washed with dry ether and dried under nitrogen. 4.22 g of a grey-brown powder were obtained. (Yield: 98% based on 3,4-diamino-2,5dibromothiophene dihydrobromide.)

This substance has a limited stability and was employed in the other reactions without further purification.

5,7-Dibromo-2,3-didecylthieno[3,4-b]pyrazine (1)

3,4-Diamino-2,5-dibromothiophene dihydrobromide (5.2 g, 12 mmol) and docosane-11,12-dione (3.4 g, 10 mmol) were mixed with one another under nitrogen in 35 ml of dichloromethane and 35 ml of absolute ethanol. Triethylamine (2.6 g, 26 mmol) was added dropwise at 0° C. to the stirred mixture, which was then kept at 60° C. for 1.5 hours. Chloroform (200 ml) was then added and a black suspension was filtered through Celite® (Manville, Filtration and Minerals™) in order to remove solids formed. The filter cake was washed with chloroform and the combined solutions were briefly stirred and warmed with active carbon. Filtration through Celite® and evaporation of the solvent under reduced pressure yielded a brown solid, which was washed with methanol and then recrystallized from this. 3.3 g (57%) of 5,7-dibromo-2,3-decylthieno[3,4-b]pyrazine were obtained as yellow needles having a melting point of 50.9° C. (decomposition).

5,7-Dibromo-2,3-dipentylthieno[3,4-b]pyrazine (11, R'=$C_5H_{11}$)

This compound was obtained in 39% yield (of theory) in a similar manner starting from dodecane-6,7-dione and 3,4-diamino-2,5-dibromothiophene dihydrobromide. It has a melting point of 103.0–103.5° C. (decomposition) (from methanol).

$^{13}$C-NMR (100 MHz, chloroform-d) δ, ppm: 13.98 ($CH_3$), 22.49, 27.51, 31.70, 25.23 ($CH_2$), 103.08 (C—Br), 139.31 (C—N), 158.08 (C=N).

3,4-Di(decanoylamino)thiophene 3,4-Diaminothiophene (2.0 g, 17 mmol) was dissolved in pyridine and the solution was added dropwise to a stirred solution of 6.5 g (34 mmol) of decanoyl chloride (boiling point 125° C. at 45 mbar) via a syringe. It was stirred overnight. The reaction mixture was poured into ice water mixed with concentrated hydrochloric acid and extracted with chloroform. The organic layers were washed with water, 2% strength NaOH and again with water and then dried over $MgSO_4$ which was mixed with active carbon to remove the colored impurities. After evaporating the solvent, a solid was obtained which was recrystallized from a toluene-hexane mixture. The solid had a melting point of 99–100° C. The yield was 6.7 g (90% of theory).

13C-NMR (100 MHz, chloroform-d) δ, ppm: 14.11 ($CH_3$), 22.69, 25.75, 29.34, 29.44, 29.53, 31.89, 36.97 ($CH_2$), 113.35 (C—H), 139.31 (C—N), 172.64 (C=O).

3,4-Di(hexadecanoylamino)thiophene

This compound was prepared in a yield of 70% of theory starting from 3,4-diaminothiophene and palmitoyl chloride (boiling point 141° C. at 1.4 mbar) in a similar manner to above. The melting point was 107–109° C. (from toluene-hexane).

3,4-Di(decanoylamino)-2,5-diiodothiophene (18, R'=C(O)$C_9H_{19}$)

The iodination process described by R. F. Heck in Organic Reactions, 27, p. 345 et seq. (1982) was used. A mixture of 1.7 g (4 mmol) of 3,4-di(decanoylamino)thiophene, 0.9 g (3.6 mmol) of iodine, 0.5 g (2.4 mmol of potassium iodate, 2.0 ml of 30% strength sulfuric acid, 12 ml of carbon tetrachloride and 7.0 ml of glacial acetic acid were stirred for two hours with warmning (75° C.). After cooling to 0° C., a precipitate was collected, washed with methanol and recrystallized from a toluene-ethanol mixture. 2.1 g (78% of theory) of 3,4-di(decanoylamino)-2,5-diiodothiophene having a melting point of 213–215° C. (decomposition) were obtained.

3,4-Di(hexadecanoylamino)-2,5-diiodothiophene (18, R'=C(O)$C_{15}H_{31}$)

This compound was prepared in a similar manner to above in a yield of 83% of theory. Its melting point was 201–203° C. (decomposition) (toluene-ethanol).

2,5-Bis(trimethvltin)thiophene (3, R=alkyl=$CH_3$) was prepared according to the process described by H. Zimmer in J. Org. Chem. 49, pp. 5250–5253 (1984).

55,5'-Bis(trimethyltin)-2,2'-bithiophene was prepared according to the process described by S. Kotani et al. in J. Organomet. Chem. 429, pp. 403–413 (1992).

5,5''-Bis(trimethyltin)-2,2':5'2''-terthiophene (VI, $R^2$=alkyl=$CH_3$)

2,2':5'2''-terthiophene (2.48 g, 10 mmol) was dissolved in dry THF. The solution was deoxygenated by passing in a gentle stream of nitrogen, cooled to −50° C., and 8.0 ml of 2.5 M n-BuLi in hexane (20 mmol) were added dropwise with stirring. The cooling bath was removed, and the reaction mixture was stirred at room temperature for a further 4 hours. Trimethyltin chloride (4.0 g 20 mmol) dissolved in 15 ml of THF was then added and the mixture was stirred overnight. The THF was evaporated, the residue was dissolved in ether, and the ether solution was washed with water and alkali solution and then dried over $MgSO_4$. The solvent was evaporated, and the solid was taken up in hexane and filtered by means of Celite®. The hexane was evaporated, and a green oil which crystallized to give a green solid was obtained. This was washed with methanol and dried over $CaCl_2$ in a desiccator. The yield was 2.8 g (50% of theory). The melting point was 107–110° C.

13C-NMR (100 MHz, chloroform-d) δ, ppm: −8.23 ($CH_3$), 124.16, 124.77, 135.91, (CH), 136.07, 137.55, 142.71 (quaternary C). $^1$H-NMR (400 MHz, chloroform-d) δ, ppm: 0.38 s (18H), 7.06 s (2H), 7.08 d (3.4 Hz, 2H), 7.27 d (3.4 Hz, 2H).

5,7-Dibromo-1,2,3,4-tetrahvdro-2,3-dioxothieno[3,4-b]pyrazine (13, X=Br)

The starting material 12 was obtained according to the process described by F. Outurquin in Bull. Chem. Soc. France, 1983, II-153–159 (process A) and crystallized from water with addition of active carbon and the evaporation of the mother liquor to a small volume. The dioxane-bromine complex (1:1, 1.75 g, 7.1 mmol) was added under nitrogen in small portions to the stirred suspension of the compound 12 (0.49 g, 2.9 mmol) in 20 ml of dry THF at −10° C. After addition was complete, the cooling bath was removed, and the reaction mixture was allowed to warm to room temperature and was stirred for 6–10 hours. A brown precipitate was filtered off, washed with ether and dried. 0.64 g (67% of theory) of a crude product of the compound 13 was obtained.

1,2,3,4-tetrahydro-5,7-diiodo-2,3-dioxothieno[3,4-b]pyrazine 13, X=I) was obtained under conditions as described by R. F. Heck starting from educt 12 (Organic Reactions, 27, 1982, p. 345; see also the preparation of 3,4-di(decanoylamino)-2,5-diiodothiophene as examplarily described above). The obtained light beige compound which exhibited an extremely low solubility in all organic solvents was obtained in sufficient purity and could be used in the subsequent reactions without further purification.

5,7-Dibromo-2,3-di(hexadecyloxy)thieno[3,4-b]pyrazine

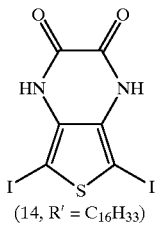

(14, R' = C$_{16}$H$_{33}$)

The starting material 13 (0.59 g, 1.8 mmol), silver carbonate (1.10 g, 4.9 mmol) and hexadecyl iodide (7.0 g, 20 mmol) were suspended in toluene (70 ml) and the mixture was kept for 30 minutes under nitrogen in an ultrasonic bath at room temperature. During the course of this, evolution of gas was observed. The reaction mixture was then stirred for 6–8 hours at 100° C. under nitrogen and kept in an ultrasonic bath (30 min, room temperature, nitrogen atmosphere). This process was repeated 6 to 8 times, the entry of bright daylight being excluded. After removing the precipitate, the dark reaction mixture was carefully filtered through Celite® under moderate vacuum and the filter cake was washed with a hexane-ether mixture until the solvent running through was colorless. The filtrate was evaporated under reduced pressure, the residue was dissolved in hexane and the solution was separated on a silica gel column. The hexadecyl iodide was eluted by means of hexane and the desired product 14 was eluted using a hexane-ether mixture (50:1). 0.56 g (40% of theory) of a pale yellow solid having a melting point of 68° C. (acetone-methanol) was obtained.

$^1$H-NMR (400 MHz, CDCl$_3$ δ, ppm): 0.88 t (6H, J 6.5 Hz, CH$_3$), 1.25 m (48H CH$_2$x24), 1.45 m (4H, CH$_2$(CH$_2$CH$_2$O)), 1.89 quint (4H, J 6.5 Hz, CH$_2$(CH$_2$O)), 4.48 t (4H, J 6.5 Hz, CH$_2$O).

$^{13}$C-NMR (100 MHz, CDC$_3$, δ, ppm): 14.33 (CH$_3$), 22.71, 25.96, 28.37, 29.31, 29.38, 29.61, 29.72 (4- to 5-fold intensity), 31.94 (CH$_2$), 67.86 (CH$_2$O), 98.63 (C—Br), 136.24 (=C(N)), 151.08 (C=N).

5,7-Dibromo-1,2-dihyro-3-methyl-2-oxothieno[3,4-b]pyrazine

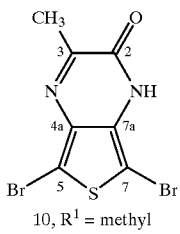

10, R$^1$ = methyl

Triethylamine (0.48 g, 4.7 mmol) was added dropwise to a stirred suspension of 3,4-diamino-2,5-dibromothienophene dihydrobromide (2.06 g, 4.7 mmol) in 30 ml water-free ethanol at 0 to 5° C. Stirring was continued at the same temperature for 30 min. Subsequently ethylpyruvate (0.58 g, 5 mmol) was added dropwise at the same temperature. The reaction mixture was allowed to warm to room temperature and was stirred for 16 h. Subsequently, it was poured into an excess of ice water, the precipitate was collected, washed with water and dried in vacuum at room temperature. Thereby, 1.05 g of a dark-brown powder was obtained. This product was used for the O-alkylation without further purification. A sample for analysis was obtained by dissolving the compound in warm chloroform, filtrating the black insoluble residues and precipitating the compound by using cold ethanol.

The substance started to degrade at temperatures of above 200° C. without melting.

$^1$H-NMR (400 MHz, DMSO-d$_6$); δ, ppm: 2.32 s (3H, CH$_3$), 11.8 br.s (1H, NH).

$^{13}$C-NMR (100 MHz, DMSO-d$_6$); δ, ppm: 20.7 (CH$_3$), 83.7 (C-7), 106.7 (C-5), 130.6 (C-4a or C-7a), 134.2 (C-7a or C-4a), 154.8 (C-2 or C-3), 159,8 (C-3 or C-2)

5,7-Dibromo-3-ethyl-1,2-dihydro-2-oxothieno[3,4-b]pyrazine

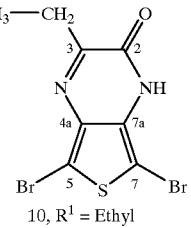

10, R$^1$ = Ethyl

Triethylamine (0.20 g, 2 mmol) was added to a stirred suspension of 3,4-diamino-2,5-dibromothiophene dihydrobromide (1.15 g, 2.66 mmol) in 20 ml water-free ethanol at 0 to 5° C. Stirring was continued at the same temperature for 30 min, and subsequently ethyl-2-oxobutanoic acid (0.27 g, 2.66 mmol) which was dissolved in 5 ml wash-free ethanol, was added dropwise. The reaction mixture was allowed to warm up to room temperature and stirring was continued for 16 h. After cooling the mixture in an ice bath the precipitate was collected, washed with cold ethanol and dried in vacuum at room temperature. Thereby 0.53 g of a dark-grey powder was obtained. This compound was used for O-alkylation without further purification. A sample for analysis was obtained by dissolving the compound in tetrahydrofurane, filtering of a black insoluble residue and precipitating the compound by cold ethanol.

Degradation was observed at temperatures of 200° C. without melting.

$^1$H-NMR (400 MHz, DMSO-d$_6$); δ, ppm: 1.20 t (3H, CH$_3$), 2.75 q (2H, CH$_2$).

$^{13}$C-NMR (100 MHz, DMSO-d$_6$); δ, ppm: 10.6 (CH$_3$), 26.5 (CH$_2$), 84.1 (C-7), 107.4 (C-5), 130.8 (C-4a or C-7a), 134.7 (C-7a or C-4a), 154.8 (C-2 or C-3), 159.8 (C-3 or C-2).

When heated (recrystallization) or on silicon dioxide a rearrangement of this substance was observed, wherein the C=N bond moved and a E/Z-mixture of 3-ethylidene-1,2,3,4-tetrahydro-2-oxothieno[3,4-b]pyrazine was obtained.

General Process for O-alkylating 1,2-dihydro-2-oxothieno[3,4-b]pyrazines (10) which are Substituted in the 3-position Synthesis of 2-alkoxy-3-alkyl(aryl)thieno[3,4-b]pyrazines (IIc)

Starting material 10 was used in amounts of several mmol. It is, however, also possible to carry out reactions in a larger range. To this starting material silver carbonate in equivalent molecular amounts and toluene (50–100 ml) were added and the reaction mixture was ultrasonicated at room temperature under nitrogen for 30 min.

(50-Subsequently alkyl iodide (10-fold excess of primary or secondary iodide) added in one batch and stirring was continued for further 10 to 20h at 60–70° C., and every 3 to 4 h it was ultrasonicated for 5 min. Subsequently, the mixture was filtered through Celite, the filter cake was washed with hexane, the filtrate was evaporated under vacuum and the product of the O-alkylation was isolated by chromatography over silica.

2-hexadecyloxy-3-methylthieno[3,4-b]pyrazine

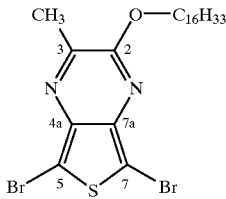

Isolation: elution with hexane from silica. Yield: 57% of the theory, mp. 58–95.5° C. (methanol-ether).

$^1$H-NMR (400 MHz, CDC$_3$); δ, ppm: 0.85 t (3H, CH$_3$ in docosyl, 1.25 s (22H, CH$_2$)$_{11}$), 1.39 m (2H, CH$_2$(CH$_2$)$_3$O), 1.49 quint (2H, CH$_2$(CH$_2$)$_2$O), 1.85 quint (2H, CH$_2$(CH$_2$O)), 2.52 s (3H, CH$_3$), 4.45 t (2H, CH$_2$O).

$^{13}$C-NMR (100 MHz, CDCl$_3$); δ, ppm: 14.13 (CH$_3$); 20.84, 22.70, 26.10, 28.51, 29.31, 29.37, 29.56, 29.60, 29.70 (5-fold intensity), 31.93, (CH$_2$-goups), 67.43 (CH$_2$O), 98.25 (C-7), 103.59 (C-5), 137.72 (C-4a or C-7a), 138.25 (C-7a or C-4a), 151.37 (C-2 or C-3), 156,73 (C-3 or C-2)

2-Docosyloxy-3-methylthieno[3,4-b]pyrazine

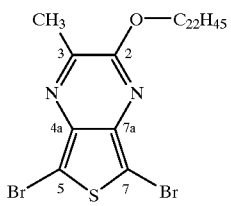

Isolation: elution from silica by means of hexane or hexane-ether (50:1).

Yield: 50% of the theory, mp. 65–67° C. (methanol-chloroform)

2-ethyl-3-hexadecyloxythieno[3,4-b]pyrazine

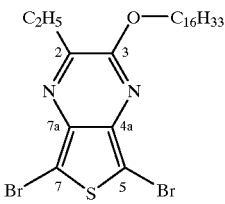

Isolation: elution from silica by means of hexane of hexane-ether (50:1).

Yield: 60% of the theory, mp. 42.5–44.5° C. (methanol-chloroform).

$^1$H-NMR (400 MHz, CDCl$_3$); δ, ppm: 0.87 t (3H, CH$_3$ in hexadecyl), 1.22 s (22H, CH$_2$)$_{11}$), 1.31 t (3H, CH$_3$(CH$_2$)), 1.39 m (2H, CH$_2$(CH$_2$)$_3$O), 1.49 quint (2H, CH$_2$(CH$_2$)$_2$O), 1.85 quint (2H, CH$_2$(CH$_2$)$_2$O), 1.85 quint (2H, CH$_2$(CH$_2$O), 2.90 q (2H, CH$_2$ in Ethyl), 4.45 t (2H, CH$_2$O).

$^{13}$C-NMR (100 MHz, CDCl$_3$); δ, ppm: 11.13 (CH$_3$), 14.13 (CH$_3$); 22.70, 26.13, 27.18, 28.52, 29.28, 29.37, 29.55, 29.58, 29.70 (5-fold intensity), 31.93, (CH$_2$-groups), 67.26 (CH$_2$O), 98.05 (C-5), 103.86 (C-7), 137.84 (C-4a or C-7a), 138.11 (C-7a or C-4a), 155.14 (C-2 or C-3), 156.46 (C-3 or C-2).

4,5,6,7-Tetrahydro-5,6-dioxocyclobuta[b]thieno[3,4-e]pyrazine (15)

3,4-Diaminothiophene (0.228 g, 2 mmol) was dissolved in absolute ethanol (4 ml) under nitrogen, and 0.359 g (2.11 mmol) of 1,2-diethoxy-3,4-dioxocyclobutene was added to the stirred solution at room temperature. The solution became yellow-brown after a few minutes, and a precipitate was formed. The mixture was stirred overnight, then the precipitate was removed and washed with a small amount of cold ethanol and ether and then dried. The yield was 0.31 g (31% of theory). The melting point was above 300° C.

$^1$H-NMR (400 MHz, DMSO-d$_6$ δ, ppm): 6.39 s (2H, H$_{ar}$), 10.73 br. s (2H, NH).

$^{13}$C-NMR (100 MHz, DMSO-d$_6$ δ, ppm): 104.32 (CH$_{ar}$), 130.45 (=C$_{ar}$(N)), 171.38 and 177.61 (C=O and =C(NH) or conversely).

1,3-Dibromo-4,5,6,7-tetrahydro-5,6-dioxocyclobuta[b]thieno[3,4-e]pyrazine (16)

Compound 15 (0.25 g, 1.3 mmol) was suspended in dry THF (5 ml). The dioxane-bromine complex (1:1, 0.78 g, 3.0 mmol) was then added in small portions at 0° C. with stirring under nitrogen. The cold bath was removed and the stirring was continued at room temperature for 6 hours. The solvent was evaporated, and the dark brown precipitate was washed first with methanol and then with ether and dried. The yield was 0.31 g (68% of theory).

$^1$H-NMR (400 MHz, DMSO-d$_6$ δ, ppm): 10.95 s (NH).

$^{13}$C-NMR (100 MHz, DMSO-d$_6$ δ, ppm): 88.56 (C—Br), 131.21 (=C$_{ar}$(N)), 171.53 and 178.08 (C=O and =C(NH) or conversely).

1,3-Dibromo-5,6-di(dodecyloxyl)cyclobuta[b]thieno[3,4-e]pyrazine (17, R'=C$_{12}$H$_{25}$)

The starting material 16 (0.20g, 0.57 mmol), silver carbonate (0.32 g, 1.20 mmol) and dodecyl iodide (3.0 g, 10 mmol) were stirred at room temperature for 3 weeks in toluene. The mixture was filtered through Celite®, the filter cake was washed with ether, and the combined solutions were evaporated, the residue was taken up in hexane and the mixture was separated on a silica gel column. The excess of dodecyl iodide was removed by means of hexane. The desired product was eluted using a hexane-ether mixture (19:1→9:1). The yield was 0.094 g (24% of theory) of a yellowish-green oil which crystallized at room temperature. The melting point was 66–67° C.

$^1$H-NMR (400 MHz, CDCl$_3$ δ, ppm): 0.87 t (6H, J 6.5 Hz, CH$_3$), 1.27 m (40H CH$_2$x20), 1.45 m (4H, CH$_2$(CH$_2$CH$_2$O)), 1.83 quint (4H, J 6.5 Hz, CH$_2$(CH$_2$O)), 4.42 t (4H, J 6.5 Hz, CH$_2$O).

$^{13}$C-NMR (100 MHz, CDCl$_3$ δ, ppm): 14.13 (CH$_3$), 22.70, 25.82, 28.41, 29.26, 29.37, 29.54, 29.59, 29.66 (4-fold intensity), 31.93 (CH$_2$), 67.12 (CH$_2$O), 108.69 (C—Br), 138.45 (=C(N)), 144.87 (>C(O)<), 164.15 (C=N).

UV (THF, $\lambda_{max}$, nm (ε)): 214 (15,300), 263 (29,100), 323 (7,800), 440 (2,400).

1,3-Dibromo-5,6-di(hexadecyloxy)cyclobuta[b]thieno[3,4-e]pyrazine (17, R'=C$_{16}$H$_{33}$)

Starting from 16 according to the process described above, this compound was prepared with the following differences. 4.3 mmol of 16, 4.3 mmol of silver carbonate and 0.1 mol of hexadecyl iodide were employed. 350 ml of toluene were used as solvent. The temperature was −40–100° C. and the reaction time was 10 days (20 ultrasonic warming cycles). The final product was isolated in the same manner as described above. The yield was 1.6 g (46% of theory) of an orange solid having a melting point of 71.5° C.

$^1$H-NMR (400 MHz, CDCl$_3$ δ, ppm): 0.83 t (6H, J 6.5 Hz, CH$_3$), 1.22 m (48H CH$_2$x24), 1.35 m (4H, CH$_2$(CH$_2$CH$_2$O)), 1.80 quint (4H, J 6.5 Hz, CH$_2$(CH$_2$O)), 4.41 t (4H, J 6.5 Hz, CH$_2$O).

$^{13}$C-NMR (100 MHz, CDCl$_3$ δ, ppm): 14.13 (CH$_3$), 22.70, 25.82, 28.41, 29.26, 29.38, 29.55, 29.60, 29.71 (4-fold intensity), 31.94 (CH$_2$)m, 67.12 (CH2O), 108.69 (C—Br), 138.46 (=C(N)), 144.88 (>C(O)<), 164.15 (C=N).

GENERAL PROCESS FOR POLYMERIZATION

Monomers of the general formula 1, 2 or mixtures thereof were used in amounts of from 1 to 2 mmol. Bis(trialkyltin) thiophenes of the general formula 3 were used in equal molar amounts (or in a 2- to 10-fold excess for the preparation of oligomers). The starting materials were dissolved in anhydrous THF (20–200 ml), introduced into a 2-necked flask which has been dried in an oven or flamed and a gentle stream of nitrogen or argon was passed through the solution for 10 to 15 minutes. From 2 to 5 mol % of bis(triphenylphosphine)palladium(II) chloride or tetrakis(triphenylphosphine)palladium(0) were added to the deoxygenated solution. The flask was fitted with a reflux condenser and the reaction was carried out under a nitrogen or argon atmosphere at from approximately 40° C. to approximately 70° C. for 1 to 7 days.

After completion of the reaction, the solvent was evaporated and the residue was dissolved off the walls of the flask by addition of methanol. The precipitate was collected, washed with methanol and hexane, the trialkyltin halides being removed. Further purification was carried out by Soxhlet extraction using methanol, hexane or acetone (for substances of low solubility). Additional purification is possible by dissolving the polymer in chloroform, THF or other solvents (if appropriate using an ultrasonic bath), centrifugation of the solution from insoluble particles (at 3000 to 5000 rpm) and the precipitation of the substances of high molecular weight by means of methanol, hexane or another suitable solvent, and subsequent centrifugation. If necessary, these purification steps can be repeated.

OLIGO- AND POLYTHIOPHENES

Example 1

2,3-Didecyl-5,7-di(2-thienyl)thieno[3,4-b]pyrazine (7)

This compound was isolated in a yield of 50% from the reaction mixture if 2,5-bis(trimethyltin)thiophene (3, n=1, R=CH$_3$) in a 10-fold molar excess and 1 (R$^1$=in each case C$_{10}$H$_{21}$) were reacted with one another. Separation was carried out on a silica gel column using hexane as eluent. The melting point of the oligomer obtained was 54–55° C.

$^1$H-NMR (400 MHz, chloroform-d) δ, ppm: 0.89 t (6H, J 7 Hz), 1.2–1.6 m (28H), 1.95 quint (4H, J 7 Hz), 2.88 t (4H, J 7 Hz), 7.08 dd (2H, H$^4$, J(4.5) 5.1 and J(4.3) 3.6 Hz), 7.33 dd (2H, H$^5$ J(5.4) 5.1 and J(5.3) 0.8 Hz), 7.58 dd (2H, H$^3$, J(3.4) 3.6 and J(3.5) 0.8 Hz).

$^{13}$C-NMR (100 MHz, chloroform-d) δ, ppm: 14.14 (CH$_3$), 22.71, 26.79, 28.48, 29.40, 29.46, 29.70 (double int.) 31.94, 34.99 (CH$_2$), 123.57 (quaternary C), 123.84 (CH), 126.05 (CH), 127.03 (CH), 134.98 (quaternary C), 137.61 (quaternary C), 156.32 (C=N).

Example 2

7-(2,2'-Bithiophen-5-yl)-2,3-didecyl-5-(2-thienyl)thieno[3,4-b]pyrazine (8)

This compound was obtained from the same reaction mixture as above in a yield of 15% of theory (eluent hexane).

$^1$H-NMR (400 MHz, chloroform-d) δ, ppm: 0.85 m (6H), 1.2–1.6 (28H), 1.95 m (4H), 2.85 m (4H), 7.04 dd (1H, J 4.1 and 4.6 Hz), 7.08 dd (1H, 3.8 and 5.0 Hz), 7.13 d (1H, J 3.8 Hz), 7.22 broad d (2H, J 4.35 Hz), 7.33 dd (1H) J 5.0 and 1.0 Hz), 7.44 d (1H, 3.8 Hz), 7.58 dd (H, J 3.8 and 1.0 Hz).

$^{13}$C-NMR (100 MHz, chloroform-d) δ, ppm: 14.14 (CH$_3$), 22.71, 26.69, 26.75, 29.40, 29.46, 29.70 (double int.), 29.88, 31.94, 34.98 (CH$_2$), 123.32 (quaternary C), 123.40, 123.66, 123.90, 124.32 (broad), 126.14, 127.06, 127.90 (CH), 133.90, 134.97, 137.66 (double int.) (quaternary C), 156.18, 156.46 (C=N).

Example 3

2,5-Bis[2,3-didecyl-7-(2-thienyl)thieno[3,4-b]pyrazin-5-yl]thiophene (9)

This compound was obtained as the main product of a reaction in which one mole equivalent of 1 (R$^1$ =C$_{10}$H$_{21}$) and three mole equivalents of 3 (n=1, R=CH$_3$) were reacted with one another. The yield was 13% of theory.

Mass spectrum (MS) (chemical ionization at normal pressure), m/z (rel. int., %): 1077.4 (50, M+), 745.2 (83), 663.3 (100), 581.3 (92), 350.0 (62), 279.1 (62).

$^1$H-NMR (400 MHz, chloroform-d) δ, ppm: 0.89 m (12H), 1.2–1.6 m 56H), 1.89 m (8H), 2.80 m(8H), 7.05 dd (2H, J 5.0 and 3.8 Hz), 7.30 dd (2H, J 5.0 and 0.9 Hz), 7.53 dd (2H, J 3.8 and 0.9 Hz), 7.61 s (2H).

$^{13}$C-NMR (100 MHz, chloroform-d) δ, ppm: 14.16 (CH$_3$), 22.74, 26.56, 26.81, 29.53, 29.83 (high int.), 29.94, 31.98, 34.92, 35.07 (CH$_2$), 123.07 (quaternary C), 123.47 (quaternary C), 123.87 (CH), 124.85 (CH), 125.80 (CH), 126.87 (CH), 135.19 (quaternary C), 137.71 and 137.91 (quaternary C), 155.81 and 156.11 (C=N).

TABLE 2

UV Spectra of the oligomers 7, 8 and 9 in THF
$\lambda_{max}$, nm($\epsilon$)

| No. | 1 | 2 | 3 | 4 | 5 |
|-----|---|---|---|---|---|
| 7 | 212 (46400) | 260 (sh) | 303 (22400) | 340 (15100) | 503 (7990) |
| 8 | 212 (36500) | 277 (15000) | 323 (13600) | 374 (18000) | 530 (133900) |
| 9 | 210 (23500) | 285 (41900) | 310 (41900) | 382 (32340) | 617 (51500) |

Example 4

Polymer 4 ($R^1 = C_5H_{11}$)

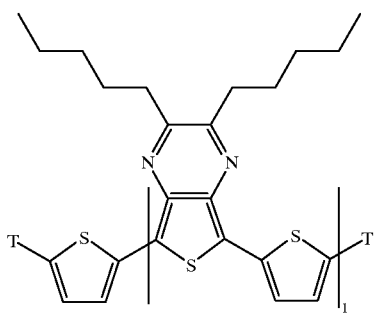

wherein T is an end group being derived from the monomers used.

This polymer was obtained according to the general process for polymerization described above starting from equimolar amounts of compound 1 ($R^1=C_5H_{11}$) and 3 (n=1, $R=CH_3$) in the presence of 5 mol % of $Pd(Ph_3P)_2Cl_2$.

The reaction time was 24 h. The reaction temperature was 65° C. Purification was carried out by Soxhlet extraction with methanol (24 h) and hexane (24 h). The yield was 39%. A black solid was obtained.

| Elemental analysis $(C_{22}H_{24}N_2S_2)_n$ | | | | |
|---|---|---|---|---|
| Calculated (%) | C 67.37, | H 6.78, | N 7.86, | S 17.99, |
| Found (%) | C 65.8, | H 6.6, | N 7.5, | S 17.6, |
| UV (THF), | c = 15 mg/l | | $\lambda_{max}$ (nm) 420 895 | $D_{max}$ 0.32 0.50 |

Color of the solution: pale green

Example 5

According to the general process for polymerization described above, starting from equimolar amounts of 5,7-dibromo-2,3-di(hexadecyloxy)thieno[3,4-b]pyrazine (1, $R^1=C_{16}H_{33}$) and 5,5'-bis(trimethyltin)-2,2'-bithiophene in the presence of 3 mol % of $Pd(Ph_3P)_2Cl_2$, after reaction at 75° C. for 24 hours and subsequent Soxhlet extraction with methanol and acetone, a polymer having recurring units of the formula below was obtained in a yield of 53% of theory.

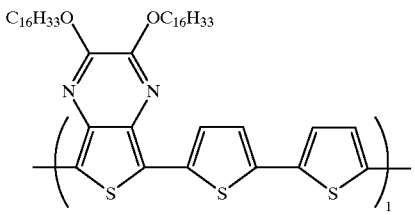

The polymer had a weight average molecular weight ($M_w$) of 29,000 and a polydispersity of 2.1, in each case measured by GPC with the aid of polystyrene as a standard. In the UV spectrum, this polymer showed a $\lambda_{max}$ of 638 nm (THF).

Example 6

In a similar manner, starting from 1,3-dibromo-5,6-di(hexadecyloxy)cyclobuta[b]thieno[3,4-e]pyrazine and 5,5'-bis(trimethyltin)-2,2'-bithiophene in the presence of 4 mol % of $Pd(Pb_3P)_2Cl_2$, after reaction at 80° C. for 36 hours and subsequent Soxhlet extraction with methanol and acetone, a polymer having the recurring units shown below was obtained in a yield of 65% of theory.

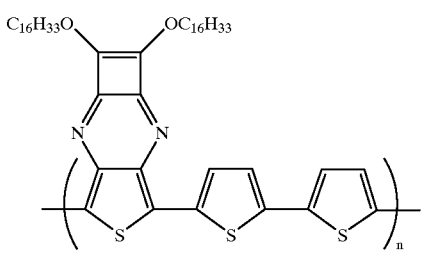

The polymer had an $M_w$ of 21,500 and a polydispersity of 2.1, in each case measured by GPC using polystyrene as a standard. The UV spectrum of the polymer exhibited values for $\lambda_{max}$ at 298 nm, 495 nm and 920 nm (THF).

What is claimed is:

1. A Polythiophene, comprising structural units of the formulae (I) and (II)

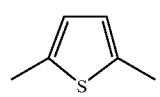
(I)

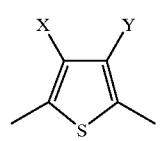
(II)

where X and Y independently of one another can be identical or different and are a linear or branched-chain $C_1$- to $C_{22}$-alkyl group; a linear or branched-chain $C_1$- to $C_{22}$-alkoxy group; a linear or branched-hain $C_1$- to $C_{22}$-acyl group; a linear or branched-chain $C_1$- to $C_{22}$-thioacyl group; a linear or branched-chain $C_1$- to $C_{22}$-acyloxy group; a linear or branched-chain $C_1$- to $C_{22}$-thioacyloxy group; a $C_5$- to $C_8$-cycloalkyl group, a $C_6$- to $C_{18}$-aryl group or a $C_5$- to $C_8$-heterocyclic group, which in each case can in turn be substituted by one or more linear or branched-chain $C_1$- to $C_{22}$-alkyl group(s), one or more linear or branched-chain $C_1$- to $C_{22}$-alkoxy group(s), one or more linear or branched-chain $C_1$- to $C_{22}$-alkoxyalkyl group(s), one or more linear or branched-chain $C_1$- to $C_{22}$-acyl group(s) or one or more linear or branched-chain $C_1$- to $C_{22}$-thioacyl group(s); $NO_2$; or $NHR^1$, where $R^1$ may be identical or different and is hydrogen or a linear or branched-chain $C_1$- to $C_{22}$-alkyl group, a linear or branched-chain $C_1$- to $C_{22}$-alkoxy group, a linear or branched-chain $C_1$- to $C_{22}$-alkoxyalkyl group, a linear or branched-chain $C_1$- to $C_{22}$-acyl group or a linear or branched-chain $C_1$- to $C_{22}$-thioacyl group, or X and Y, together with the atoms to which they are bonded, form a carbon-containing ring system which beside carbon contains nitrogen (N), oxygen (O), sulfur (S) or phosphorus (P) heteroatoms or mixtures of two or more of these heteroatoms, where this ring system can in turn be substituted on the carbon atom(s), the nitrogen atom(s) or the phosphorus atom(s) in each case by a group Z, where each Z independently of one another is a group as defined above for X and Y, or two adjacent groups Z together form a radical represented by one of the following formulae (III) to (VI)

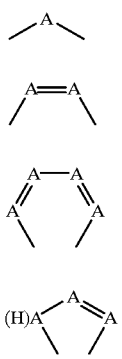

where A is carbon (C), nitrogen (N), phosphorus (P) or mixtures of two or more of these atoms, where, if A is carbon, each of these As can either carry a hydrogen atom or can in turn be substituted as defined above for X and Y, obtainable by the Stille reaction, wherein 2,5-dihalothiophene or 2,5-ditriflatethiophene and thiophene derivatives which are bis(trialkyltin)-substituted on the carbon atoms adjacent to the sulfur, which correspond to the structural unit (II) defined above, or 2,5 bis(trialkyltin) thiophene and thiophene derivatives which are bis(halo)- or bis(triflate)-substituted on the carbon atoms adjacent to the sulfur, which correspond to the structural unit (II) defined above, are reacted with one another in suitable solvents in the presence of suitable Pd(0) or Pd(II) complexes or salts thereof as catalyst, or the Suzuki reaction, wherein 2,5-dihalo- or 2,5-triflate-substituted thiophenes, which correspond to the structural unit (II) according to the invention, are reacted with thiophenediboric acid or thiophenediboric acid esters in the presence of a base and of a palladium complex of the structure $PdL_4$ (L=ligand), wherein the diboric acid (ester) derivatives of the thiophene derivatives corresponding to the above structural units (II) are reacted with 2,5-dihalo- or 2,5-triflate-substituted thiophene in the presence of a base and a palladium complex, as defined above.

2. A polythiophene as defined in claim 1, comprising structural units of the formula (VII) or (VIII)

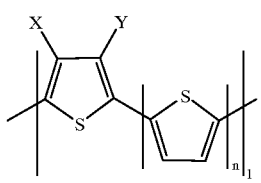

(VII)

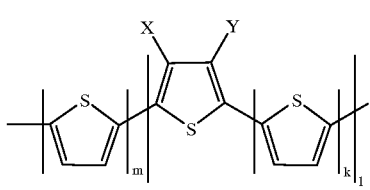

(VIII)

or mixtures of these in which X and Y are as defined in claim 1, n, m and k each independendly of one another are an integer from 1 to 10, and 1 is an integer from 1 to 3000.

3. A polythiophene as defined in claim 1 or 2, in which the structural unit (II) is selected from the group consisting of the radicals of the following formulae

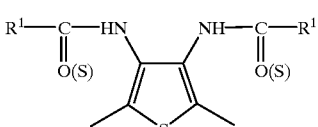

(IIa)

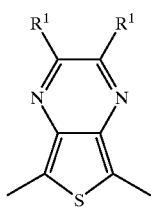

(IIb)

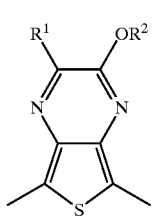

(IIc)

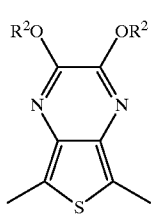

(IId)

-continued

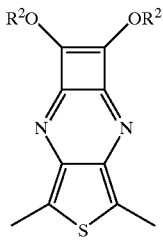

(IIe)

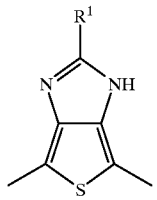

(IIf)

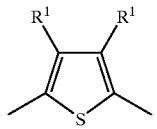

(IIg)

and mixtures of these, in which $R^1$ is as defined in claim 1 and $R^2$ is $CHR^1_2$ or $CH_2R^1$, under the proviso that radicals of formula (IIg), wherein $R^1$ represent hydrogen, are excluded.

4. A process for preparing a polythiophene, which comprises reacting 2,5-dihalothiophene or 2,5-ditriflatethiophene and thiophene derivatives which are bis (trialkyltin)-substituted on the carbon atoms adjacent to the sulfur, which correspond to the structural unit (II) defined in claim 1, with one another in suitable solvents in the presence of suitable Pd(0) or Pd(II) complexes as catalyst.

5. A process for preparing a polythiophene, which comprises reacting 2,5-bis(trialkyltin)thiophene and thiophene derivatives which are bis(halogen)- or bis(triflate)-substituted on the carbon atoms adjacent to the sulfur, which correspond to the structural units (II) defined in claim 1, with one another in suitable solvents in the presence of suitable Pd(0) or Pd(II) complexes as catalyst.

6. Antistatic finishing of substances which do not or only poorly conduct electrical current, electrically conductive films, semiconductor films, additive for active electrodes, LEDs, organic transistors; or capacitors, each respectively comprising undoped or doped polythiophenes as claimed in claims 1 to 3.

7. A process for the antistatic finishing of substances which do not or only poorly conduct electrical current by applying a layer comprising an electrically conductive organic polymer to the surface of the substrate, which comprises producing on the surface of the substrates by polymerization a layer of at least one polythiophene which contains structural units of the formulae (I) and (II) as defined in claim 1.

8. An electrically conductive material, comprising at least one polythiophene as defined in at least one of claims 1 to 3.

9. A polythiophene obtained by the process of claim 4.

10. A polythiophene obtained by the process of claim 5.

11. A polythiophene as claimed in claim 1, wherein the polythiophene is essentially undoped.

\* \* \* \* \*

UNITED STATES PATENT AND TRADEMARK OFFICE
CERTIFICATE OF CORRECTION

PATENT NO. : 6,242,561 B1
DATED : June 5, 2001
INVENTOR(S) : Möhwald et al.

It is certified that error appears in the above-identified patent and that said Letters Patent is hereby corrected as shown below:

Title page,
Item [54], the title should read:
SUBSTITUTED POLYTHIOPHENES, PROCESSES FOR THEIR PREPARATION AND THEIR USE.

Column 30, claim 1,
Line 42, "Polythiophene" should be -- polythiophene --.
Line 60, "branched-hain" should be -- branched-chain --; and "$C_{22}$-acyl" should be -- $C_{22}$-alkoxyalkyl --.
Line 61, after "group;" insert -- a linear or branched chain $C_1$-$C_{22}$-acyl group; --.

Column 31, claim 1,
Lines 20, 45, and 53, "defmed" should be -- defined --.

Column 32, claim 3,
Line 30, delete "or 2".

Column 34, claim 8,
Lines 27-28, delete "to 3".

Signed and Sealed this

Thirteenth Day of November, 2001

Attest:

*Nicholas P. Godici*

NICHOLAS P. GODICI
*Attesting Officer*  *Acting Director of the United States Patent and Trademark Office*